(12) United States Patent
Watanabe et al.

(10) Patent No.: US 10,474,050 B2
(45) Date of Patent: Nov. 12, 2019

(54) TONER AND CHARGE CONTROL AGENT USING PYRAZOLONE DERIVATIVE OR SALT OF DERIVATIVE

(71) Applicant: HODOGAYA CHEMICAL CO., LTD., Tokyo (JP)

(72) Inventors: Jun Watanabe, Ibaraki (JP); Masaya Tojo, Tokyo (JP); Hideyuki Otsuka, Ibaraki (JP)

(73) Assignee: HODOGAYA CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 15/760,954

(22) PCT Filed: Sep. 8, 2016

(86) PCT No.: PCT/JP2016/076368
§ 371 (c)(1),
(2) Date: Mar. 16, 2018

(87) PCT Pub. No.: WO2017/047482
PCT Pub. Date: Mar. 23, 2017

(65) Prior Publication Data
US 2018/0275546 A1 Sep. 27, 2018

(30) Foreign Application Priority Data
Sep. 17, 2015 (JP) ................... 2015-184475

(51) Int. Cl.
*G03G 9/097* (2006.01)
*C07D 231/22* (2006.01)
*C07D 231/32* (2006.01)
*C07D 231/20* (2006.01)
*G03G 9/087* (2006.01)

(52) U.S. Cl.
CPC ........ *G03G 9/09758* (2013.01); *C07D 231/20* (2013.01); *C07D 231/22* (2013.01); *C07D 231/32* (2013.01); *G03G 9/097* (2013.01); *G03G 9/08711* (2013.01); *G03G 9/08755* (2013.01)

(58) Field of Classification Search
CPC ........... G03G 9/09783; G03G 9/09758; C07D 231/22; C07D 231/20; C07D 231/32
See application file for complete search history.

(56) References Cited

U.S. PATENT DOCUMENTS

| | | | |
|---|---|---|---|
| 4,070,536 A | 1/1978 | Konotsune et al. |
| 4,206,064 A | 6/1980 | Kiuchi et al. |
| 4,338,390 A | 7/1982 | Lu |
| 4,391,890 A | 7/1983 | Lu |
| 4,394,430 A | 7/1983 | Jadwin et al. |
| 4,403,027 A | 9/1983 | Ishikawa et al. |
| 4,767,688 A | 8/1988 | Hashimoto et al. |
| 5,049,467 A | 9/1991 | Yamanaka |
| 2015/0220013 A1 | 8/2015 | Nishikawa et al. |

FOREIGN PATENT DOCUMENTS

| | | | |
|---|---|---|---|
| CH | 605796 A5 | * 10/1978 | ........... C07D 213/26 |
| EP | 0227874 A1 | 7/1987 | |
| EP | 0242420 A1 | 10/1987 | |
| EP | 0712049 B1 | 7/2001 | |
| JP | S55-113706 A | 9/1980 | |
| JP | 55-042752 B2 | 11/1980 | |
| JP | S57-111541 A | 7/1982 | |

(Continued)

OTHER PUBLICATIONS

Marchetti, F.; Pettinari, C.; Pettinari, R. Acylpyrazolone ligands: Synthesis, structures, metal coordination chemistry and applications. Coordination Chemistry Reviews 249 (2005) 2909-2945.*
Marchetti, F. et al. Organotin(IV) derivatives of novel betadiketones Part V. (abbreviated title) Journal of Organometallic Chemistry 645 (2002) 134-145.*
Marchetti, F.; Pettinari, C.; Pettinari, R. Recent advances in acylpyrazolone metal complexes and their potential applications. Coordination Chemistry Reviews 303 (2015) 1-31.*
Marchetti, F. et al. Synthesis and characterization of novel oxovanadium(IV) complexes with 4-acyl-5-pyrazolone donor ligands: Evaluation of their catalytic activity for the oxidation of styrene derivatives. Applied Catalysis A: General 378 (2010) 211-220.*
International Search Report in International Application No. PCT/JP2016/076368, filed Sep. 17, 2015.
Bunseki Kagaku, May 14, 1990, 39:559-565.

(Continued)

*Primary Examiner* — Christopher D Rodee
(74) *Attorney, Agent, or Firm* — Saliwanchik, Lloyd & Eisenschenk

(57) ABSTRACT

The purpose of the present invention is to provide a charge control agent for polymerized toners and particularly for color toners, which has a large charge amount and environmentally stable charging characteristics.

Since a charge control agent including a pyrazolone derivative represented by a general formula (1) or a salt of the derivative as an active ingredient has a large charge amount and excellent environmental stability of charging, it has an excellent charge-imparting effect for use in polymerized toners and particularly in color toners:

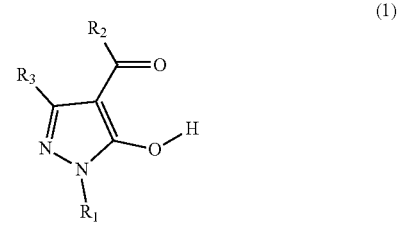

(1)

in the formula, $R_1$, $R_2$, and $R_3$ each independently represent a substituted or unsubstituted C1 to C20 linear or branched alkyl group, a substituted or unsubstituted aromatic hydrocarbon group, a substituted or unsubstituted aromatic heterocyclic group, or a substituted or unsubstituted condensed polycyclic aromatic group.

4 Claims, No Drawings

(56) References Cited

FOREIGN PATENT DOCUMENTS

| JP | S57-119364 A | 7/1982 |
|---|---|---|
| JP | 58-009154 A | 1/1983 |
| JP | S58-98742 A | 6/1983 |
| JP | 60-193689 A | 10/1985 |
| JP | 61-003149 A | 1/1986 |
| JP | S61-69073 A | 4/1986 |
| JP | 61-141453 A | 6/1986 |
| JP | 61-221756 A | 10/1986 |
| JP | S62-94856 A | 5/1987 |
| JP | 01-306861 A | 12/1989 |
| JP | 2568675 B2 | 1/1997 |
| JP | 2899038 B2 | 6/1999 |
| JP | 2001-523014 A | 11/2001 |
| JP | 3313871 B2 | 8/2002 |
| JP | 3325730 B2 | 9/2002 |
| JP | 3359657 B2 | 12/2002 |
| JP | 2003-162100 A | 6/2003 |
| JP | 2003-295522 A | 10/2003 |
| JP | 2010-211233 A | 9/2010 |
| JP | 2014-078003 A | 5/2014 |
| WO | WO-99/24871 A1 | 5/1999 |
| WO | WO-99/24873 A1 | 5/1999 |
| WO | WO-2007/111346 A1 | 10/2007 |
| WO | WO-2007/119797 A1 | 10/2007 |
| WO | WO-2014/049347 A1 | 4/2014 |

OTHER PUBLICATIONS

Waldmann-Meyer, Heinz et al., Determination of Free Protein Mobilities by Paper Electrophoresis with Evaporation, Acta Chemica Scandinavica, 1959, 13(1):13-28.

Partial English Translation of Bunseki Kagaku, "Proton and carbon-13 nuclear magnetic resonance of 4-acyl-5-pyrazolone derivative and divalent metal complex," May 14, 1990, 39:559-565.

Supplementary European Search Report dated Jan. 14, 2019 in European Application No. 16846353.7.

Khan, M. A. et al., "Pyranopyrazoles III Synthesis of 1H-Pyrano[2,3-c]pyrazol-4-ones [1]," *Journal of Heterocyclic Chemistry*, Jan. 2001, 38:193-197.

Elo, P. et al., "Titanium complexes with modifiable pyrazolonato and pyrazolonato-ketimine ligands: Synthesis, characterization and ethylene polymerization behavior," *Journal of Organometallic Chemistry*, Sep. 29, 2009, 695:11-17, Elsevier B.V.

* cited by examiner

TONER AND CHARGE CONTROL AGENT USING PYRAZOLONE DERIVATIVE OR SALT OF DERIVATIVE

CROSS-REFERENCE TO RELATED APPLICATIONS

This application is the U.S. national stage application of International Patent Application No. PCT/JP2016/076368, filed Sep. 8, 2016, which claims priority to Japanese Application No. 2015-184475, filed Sep. 17, 2015, the disclosures of each of which are incorporated herein by reference in their entirety.

TECHNICAL FIELD

The present invention relates to a charge control agent used in an image forming apparatus for visualizing an electrostatic latent image in fields of electrophotography, electrostatic recording, and the like, and a negatively-charged toner including charge control agent.

BACKGROUND ART

In an image forming process using an electrophotographic method, an electrostatic latent image is formed on an inorganic photoreceptor such as selenium, selenium alloy, cadmium sulfide, and amorphous silicon or an organic photoreceptor using a charge generating agent and a charge transporting agent, and the formed image is developed by a toner, transferred to a paper or a plastic film, and fixed to obtain a visible image.

As for the photoreceptors, depending on the composition, there are those positively charged and those negatively charged. In the case of forming printing parts as an electrostatic latent image by exposure, the image is developed by a toner having an opposite sign electrical charge. Meanwhile, in the case of reversely developing printing parts by removing the electricity of the printing parts, the image is developed by a toner having a same sign electrical charge. A toner is constituted of binder resin, a coloring agent, and other additives, and a charge control agent is usually used therein to provide desired frictional charge characteristics (charge speed, charge level, charge stability, and the like), temporal stability, and environmental stability. This charge control agent largely affects the characteristics of the toner.

Further, in the case of color toners, a light-colored charge control agent, desirably colorless charge control agent, which does not affect the hue is needed. Examples of these light-colored or colorless charge control agents include metal complex salt compounds of hydroxybenzoic acid derivatives (see Patent Literatures 1 to 3), aromatic dicarboxylic acid metal salt compounds (see Patent Literature 4), metal complex salt compounds of anthranilic acid derivatives (see Patent Literatures 5 and 6), organic boron compounds (see Patent literatures 7 and 8), biphenol compounds (see Patent Literature 9), calix[n] arene compounds (see Patent Literatures 10 to 15), and cyclic phenol sulfides (see patent Literatures 16 to 18) for a negatively charged toner, and quaternary ammonium salt compounds (see Patent Literatures 19 to 21) for a positively charged toner.

CITATION LIST

Patent Literature

Patent Literature 1: Japanese Examined Patent Publication No. 55-042752
Patent Literature 2: Japanese Patent Application Laid-open No. 61-069073
Patent Literature 3: Japanese Patent Application Laid-open No. 61-221756
Patent Literature 4: Japanese Patent Application Laid-open No. 57-111541
Patent Literature 5: Japanese Patent Application Laid-open No. 61-141453
Patent Literature 6: Japanese Patent Application Laid-open No. 62-094856
Patent Literature 7: U.S. Pat. No. 4,767,688
Patent Literature 8: Japanese Patent Application Laid-open No. 1-306861
Patent Literature 9: Japanese Patent Application Laid-open No. 61-003149
Patent Literature 10: Japanese Patent No. 2568675
Patent Literature 11: Japanese Patent No. 2899038
Patent Literature 12: Japanese Patent No. 3359657
Patent Literature 13: Japanese Patent No. 3313871
Patent Literature 14: Japanese Patent No. 3325730
Patent Literature 15: Japanese Patent Application Laid-open No. 2003-162100
Patent Literature 16: Japanese Patent Application Laid-open No. 2003-295522
Patent Literature 17: WO2007-111346
Patent Literature 18: WO2007-119797
Patent Literature 19: Japanese Patent Application Laid-open No. 57-119364
Patent Literature 20: Japanese Patent Application Laid-open No. 58-009154
Patent Literature 21: Japanese Patent Application Laid-open No. 58-098742
Non-Patent Literature 1: BUNSEKI KAGAKU, Vol 39, 564 (1990)
Non-Patent Literature 2: Acta Chem. Scand. 13 (1959) No. 8

SUMMARY OF INVENTION

Problem to be Solved by the Invention

However, many of these charge control agents have disadvantages, e.g., a charge rising speed is slow, there is a problem in the environmental stability of the charge amount at high temperature and high humidity and the charge amount itself is low, many toners including these charge control agents are reversely charged toners, and the dispersibility or stability of the compound is low. Further, for example, they cannot be applied to a polymerized toner, and thus, there has been no one having satisfactory performance as a charge control agent.

In view of the circumstances described above, it is an object of the present invention to provide a charge control agent including a pyrazolone derivative or a salt of the derivative as an active ingredient, which is useful particularly for color toners and further for polymerized toners and has a large charge amount and charging characteristics particularly excellent in the environmental stability. Further, it is an object to provide a negatively charged toner that uses the charge control agent and has high charging performance.

Means for Solving the Problem

The present invention is obtained by finding that a pyrazolone derivative or a salt of the derivative has a particularly excellent charge-imparting effect as a result of conducting intensive studies in order to achieve the above-mentioned objects, and summarized as follows.

1. The present invention relates to a charge control agent characterized by including a pyrazolone derivative represented by a general formula (1) or a salt of the derivative as an active ingredient.

[Chem. 1]

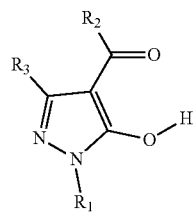

(1)

(In the formula, $R_1$, $R_2$, and $R_3$ each independently represent a substituted or unsubstituted C1 to C20 linear or branched alkyl group, a substituted or unsubstituted aromatic hydrocarbon group, or a substituted or unsubstituted condensed polycyclic aromatic group).

2. The present invention relates to the charge control agent characterized in that in the general formula (1), $R_1$, $R_2$, and $R_3$ each independently represent a substituted or unsubstituted aromatic hydrocarbon group, a substituted or unsubstituted aromatic heterocyclic group, or a substituted or unsubstituted condensed polycyclic aromatic group.

3. The present invention relates to the charge control agent characterized in that in the general formula (1), $R_1$, $R_2$, and $R_3$ each independently represent a substituted or unsubstituted aromatic hydrocarbon group.

4. The present invention relates to the charge control agent characterized in that the salt of the pyrazolone derivative is a zinc (Zn) salt, an aluminum (Al) salt, a zirconium (Zr) salt, an iron (Fe) salt, a barium (Ba) salt, or a vanadium (V) salt.

5. Further, the present invention relates to a toner, including: a charge control agent including the pyrazolone derivative or a salt of the derivative as an active agent; a coloring agent; and binder resin.

Effects of the Invention

In the present invention, the charge control agent including the pyrazolone derivative represented by the general formula (1) or the salt of the derivative as an active ingredient has the charge amount larger than that of an existing charge control agent and charging characteristics particularly excellent in the environmental stability. Further, since it is completely colorless, it is optimal for color toners and particularly for polymerized toners, and excellent in the dispersibility or the stability of the compound.

MODES FOR CARRYING OUT THE INVENTION

A pyrazolone derivative represented by a general formula (1) or a salt of the derivative, which is used in the present invention, can be produced by performing a well-known substitution reaction or a metalation reaction following the well-known substitution reaction (see, for example, Non-Patent Literatures 1 and 2).

Specific examples of "a linear or branched C1 to C20 alkyl group" in "a substituted or unsubstituted C1 to C20 linear or branched alkyl group" represented by $R_1$, $R_2$, and $R_3$ in the general formula (1) include groups such as a methyl group, an ethyl group, an n-propyl group, a 2-propyl group, an n-butyl group, a sec-butyl group, a 2-methylpropyl group, a tert-butyl group, an n-pentyl group, a 1-methylbutyl group, a 1-ethylpropyl group, a 1,1-dimethylpropyl group, a 1,2-dimethylpropyl group, an n-hexyl group, a 1-methylpentyl group, a 2-methylpentyl group, a 3-methylpentyl group, a 4-methylpentyl group, a 1-ethylbutyl group, a 2-ethylbutyl group, a 1,1-dimethylbutyl group, a 1,2-dimethylbutyl group, a 1,3-dimethylbutyl group, a 1,4-dimethylbutyl group, a 2,2-dimethylbutyl group, a 2,3-dimethylbutyl group, a 3,3-dimethylbutyl group, a 1-ethyl-2-methylpropyl group, a 1,1,2-trimethylpropyl group, an n-heptyl group, a 2-methylhexyl group, an n-octyl group, an isooctyl group, a tert-octyl group, a 2-ethylhexyl group, a 3-methylheptyl group, an n-nonyl group, an isononyl group, a 1-methyloctyl group, a 2-ethylheptyl group, an n-decyl group, a 1-methylnonyl group, an n-undecyl group, a 1,1-dimethylnonyl group, an n-dodecyl group, an n-tetradecyl group, an n-heptadecyl group, and an n-octadecyl group.

Specific examples of "a substituted group" in "a substituted or unsubstituted C1 to C20 linear or branched alkyl group" represented by $R_1$, $R_2$, and $R_3$ in the general formula (1) include groups such as a fluorine atom, a chlorine atom, a cyano group, a hydroxyl group, a nitro group, a cyclopentyl group, a cyclohexyl group, a linear or branched C1 to C6 alkoxy group, a dialkylamino group substituted with a linear or branched C1 to C6 alkyl group, a linear or branched C1 to C20 acyl group, a linear or branched C1 to C20 alkoxycarbonyl group, a C1 to C6 epoxyalkyl group, a phenyl group, a naphthyl group, an anthryl group, a fluorenyl group, a styryl group, a pyridyl group, a pyridoindolyl group, a quinolyl group, and a benzothiazolyl group, and these substitution groups may be further substituted.

Specific examples of "an aromatic hydrocarbon group" or "a condensed polycyclic aromatic group" in "a substituted or unsubstituted aromatic hydrocarbon group" or "a substituted or unsubstituted condensed polycyclic aromatic group" represented by $R_1$ in the general formula (1) include groups such as a phenyl group, a biphenylyl group, a terphenylyl group, a naphthyl group, an anthryl group, a phenanthryl group, a fluorenyl group, an indenyl group, and a pyrenyl group.

Specific examples of "a substitution group" in "a substituted aromatic hydrocarbon group" or "a substituted condensed polycyclic aromatic group" represented by $R_1$ in the general formula (1) include groups such as a fluorine atom, a chlorine atom, a cyano group, a hydroxyl group, a nitro group, a linear or branched C1 to C6 alkyl group, a cyclopentyl group, a cyclohexyl group, a linear or branched C1 to C6 alkoxy group, a dialkylamino group substituted with a linear or branched C1 to C6 alkyl group, a phenyl group, a naphthyl group, an anthryl group, a fluorenyl group, a styryl group, a pyridyl group, a pyridoindolyl group, a quinolyl group, and a benzothiazolyl group, and these substitution groups may be further substituted.

Specific examples of "an aromatic hydrocarbon group", "an aromatic heterocyclic group", or "a condensed polycyclic aromatic group" in "substituted or unsubstituted aromatic hydrocarbon group", "substituted or unsubstituted aromatic heterocyclic group", or "substituted or unsubstituted condensed polycyclic aromatic group" represented by $R_2$ in the general formula (1) include groups such as a phenyl group, a biphenylyl group, a terphenylyl group, a naphthyl group, an anthryl group, a phenanthryl group, a fluorenyl group, an indenyl group, a pyrenyl group, a pyridyl group, a triazyl group, a pyrimidyl group, a furanyl group, a pyranyl group, a thiophenyl group, a quinolyl group, an isoquinolyl group, a benzofuranyl group, a benzothiophenyl group, an indolyl group, a carbazolyl group, a benzoxazolyl group, a benzothiazolyl group, a quinoxalyl group, a benzimidazolyl group, a pyrazolyl group, a dibenzofuranyl group, a dibenzothiophenyl group, a naphthyridinyl group, a phenanthrolinyl group, and an acridinyl group.

Specific examples of "a substitution group" in "substituted aromatic hydrocarbon group", "substituted aromatic heterocyclic group", or "substituted condensed polycyclic aromatic group" represented by $R_2$ in the general formula (1) include groups such as a fluorine atom, a chlorine atom, a cyano group, a hydroxyl group, a nitro group, a linear or branched C1 to C6 alkyl group, a cyclopentyl group, a cyclohexyl group, a linear or branched C1 to C6 alkoxy group, a dialkylamino group substituted with a linear or branched C1 to C6 alkyl group, a phenyl group, a naphthyl group, an anthryl group, a fluorenyl group, a styryl group, a pyridyl group, a pyridoindolyl group, a quinolyl group, a benzothiazolyl group, and a tenoyl group, and, these substitution groups may be further substituted.

The salt of the pyrazolone derivative according to the present invention is produced by performing salt exchange reaction between a pyrazolone derivative and a metal salt or a complex reaction, for example. Although not particularly limited, any of an inorganic metal salt and an organic metal salt can be used as long as it is nontoxic. Examples of the salt include a lithium (Li) salt, a sodium (Na) salt, a potassium (K) salt, a silver (Ag) salt, a copper (Cu) salt, a magnesium (Mg) salt, a calcium (Ca) salt, a barium (Ba) salt, a zinc (Zn) salt, an iron (Fe) salt, a cobalt (Co) salt, a manganese (Mn) salt, an aluminum (Al) salt, a zirconium (Zr) salt, and a vanadium (V) salt.

The number of positive charges of the metal ion or the metal oxide ion of the salt of the pyrazolone derivative is preferably 2 to 6. When the number of positive charges of the metal ion is not less than 6, the complex compound becomes unstable and the performance as a charge control agent also becomes unstable. In order to form a more stable complex, metal ions of $Zn^{2+}$, $Al^{3+}$, $Zr^{4+}$, $Fe^{2+}$, $Fe^{3+}$, $Ca^{2+}$, $Cr^{2+}$, $Cu^{2+}$, $Co^{2+}$, and the like, or metal oxide ions of $V(O)^{2+}$, $Zr(O)^{2+}$, and the like whose number of positive charges are 2 to 4, are more preferable.

Further, in the case of the pyrazolone derivative represented by the general formula (1), it is possible to provide a safe pyrazolone derivative that includes no metal, particularly hazardous metal such as chromium, does not easily cause ignition or explosion unlike a compound including a nitro group, and is excellent in the performance as a charge control agent as compared with an existing pyrazolone monoazo iron complex compound.

Specific examples include the following examples of compounds No. 1 to 95.

[Chem. 2]

(Example compound No. 1)

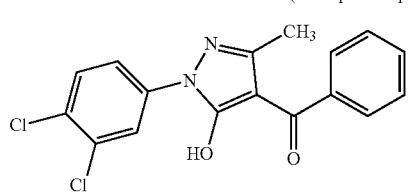

[Chem. 3]

(Example compound No. 2)

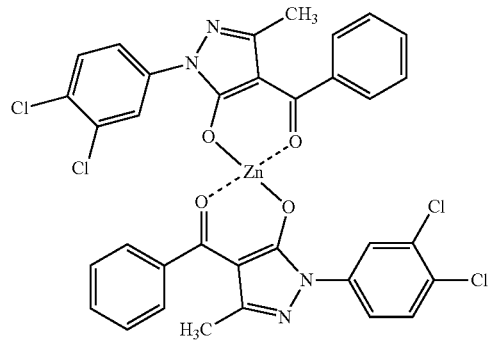

[Chem. 4]

(Example compound No. 3)

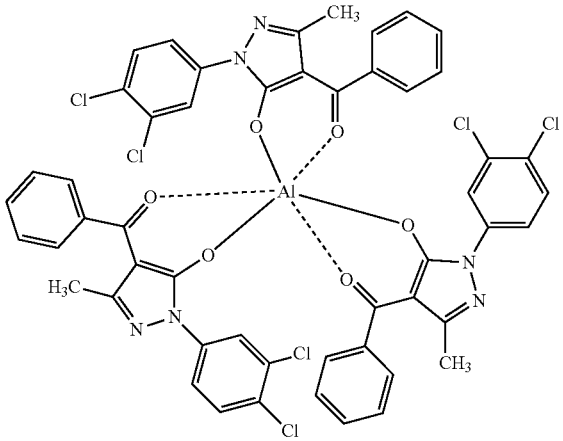

[Chem. 5]

(Example compound No. 4)

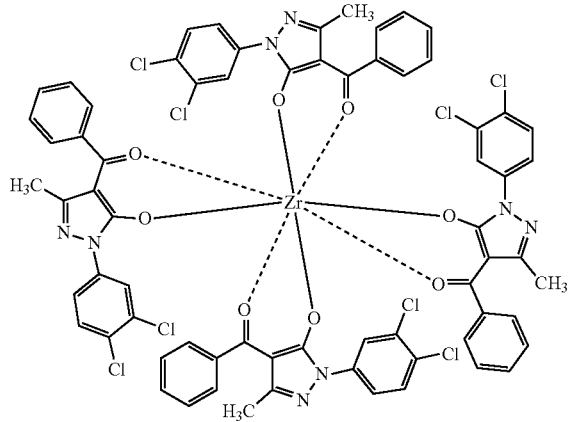

TABLE 1

|  | R$_1$ | R$_2$ | R$_3$ | Metal ion of salt |
|---|---|---|---|---|
| Example compound No. 5 | 3,4-Cl$_2$-C$_6$H$_3$ | C$_6$H$_5$ | CH$_3$ | Ca$^{2+}$ |
| Example compound No. 6 | 3,4-Cl$_2$-C$_6$H$_3$ | C$_6$H$_5$ | CH$_3$ | Fe$^{3+}$ |
| Example compound No. 7 | 3,4-Cl$_2$-C$_6$H$_3$ | C$_6$H$_5$ | H | Zn$^{2+}$ |
| Example compound No. 8 | 3,4-Cl$_2$-C$_6$H$_3$ | C$_6$H$_5$ | CH$_2$CH$_2$CH$_3$ | Zn$^{2+}$ |
| Example compound No. 9 | 3,4-Cl$_2$-C$_6$H$_3$ | C$_6$H$_5$ | C$_6$H$_5$ | Zn$^{2+}$ |
| Example compound No. 10 | C$_6$H$_5$ | C$_6$H$_5$ | CH$_3$ | — |
| Example compound No. 11 | C$_6$H$_5$ | C$_6$H$_5$ | CH$_3$ | Zn$^{2+}$ |
| Example compound No. 12 | C$_6$H$_5$ | C$_6$H$_5$ | CH$_3$ | Al$^{3+}$ |
| Example compound No. 13 | C$_6$H$_5$ | C$_6$H$_5$ | CH$_3$ | Zr$^{4+}$ |
| Example compound No. 14 | C$_6$H$_5$ | C$_6$H$_5$ | CH$_3$ | Cd$^{2+}$ |
| Example compound No. 15 | C$_6$H$_5$ | C$_6$H$_5$ | CH$_3$ | Sn$^{2+}$ |
| Example compound No. 16 | C$_6$H$_5$ | C$_6$H$_5$ | CH$_3$ | Pd$^{2+}$ |
| Example compound No. 17 | C$_6$H$_5$ | 4-t-Butyl-C$_6$H$_4$ | CH$_3$ | — |
| Example compound No. 18 | C$_6$H$_5$ | 4-t-Butyl-C$_6$H$_4$ | CH$_3$ | Zn$^{2+}$ |
| Example compound No. 19 | C$_6$H$_5$ | 4-Cl—C$_6$H$_4$ | CH$_3$ | — |
| Example compound No. 20 | C$_6$H$_5$ | 4-Cl—C$_6$H$_4$ | CH$_3$ | Zn$^{2+}$ |
| Example compound No. 21 | C$_6$H$_5$ | 4-Cl—C$_6$H$_4$ | CH$_3$ | Zr$^{4+}$ |
| Example compound No. 22 | C$_6$H$_5$ | 4-CH$_3$—C$_6$H$_4$ | CH$_3$ | — |
| Example compound No. 23 | C$_6$H$_5$ | 4-OCH$_3$—C$_6$H$_4$ | CH$_3$ | — |
| Example compound No. 24 | C$_6$H$_5$ | 4-CF$_3$—C$_6$H$_4$ | CH$_3$ | — |
| Example compound No. 25 | C$_6$H$_5$ | 4-CF$_3$—C$_6$H$_4$ | CH$_3$ | Zn$^{2+}$ |
| Example compound No. 26 | C$_6$H$_5$ | 4-CF$_3$—C$_6$H$_4$ | CH$_3$ | Al$^{3+}$ |
| Example compound No. 27 | C$_6$H$_5$ | 4-CF$_3$—C$_6$H$_4$ | CH$_3$ | Zr$^{4+}$ |
| Example compound No. 28 | 3,4-Cl$_2$—C$_6$H$_3$ | 4-Cl—C$_6$H$_4$ | CH$_3$ | — |
| Example compound No. 29 | 3,4-Cl$_2$—C$_6$H$_3$ | 4-Cl—C$_6$H$_4$ | CH$_3$ | Zn$^{2+}$ |
| Example compound No. 30 | 3,4-Cl$_2$—C$_6$H$_3$ | 4-Cl—C$_6$H$_4$ | CH$_3$ | Al$^{3+}$ |
| Example compound No. 31 | 3,4-Cl$_2$—C$_6$H$_3$ | 4-Cl—C$_6$H$_4$ | CH$_3$ | Zr$^{4+}$ |
| Example compound No. 32 | 3,4-Cl$_2$—C$_6$H$_3$ | 4-CF$_3$—C$_6$H$_4$ | CH$_3$ | — |
| Example compound No. 33 | 3,4-Cl$_2$—C$_6$H$_3$ | 4-CF$_3$—C$_6$H$_4$ | CH$_3$ | Zn$^{2+}$ |
| Example compound No. 34 | 3,4-Cl$_2$—C$_6$H$_3$ | 4-CF$_3$—C$_6$H$_4$ | CH$_3$ | Al$^{3+}$ |
| Example compound No. 35 | 3,4-Cl$_2$—C$_6$H$_3$ | 4-CF$_3$—C$_6$H$_4$ | CH$_3$ | Zr$^{4+}$ |
| Example compound No. 36 | 3,4-Cl$_2$—C$_6$H$_3$ | 4-OCH$_3$—C$_6$H$_4$ | CH$_3$ | — |
| Example compound No. 37 | 3,4-Cl$_2$—C$_6$H$_3$ | 4-OCH$_3$—C$_6$H$_4$ | CH$_3$ | Zn$^{2+}$ |
| Example compound No. 38 | 3,4-Cl$_2$—C$_6$H$_3$ | 4-OCH$_3$—C$_6$H$_4$ | CH$_3$ | Al$^{3+}$ |
| Example compound No. 39 | 3,4-Cl$_2$—C$_6$H$_3$ | 4-OCH$_3$—C$_6$H$_4$ | CH$_3$ | Zr$^{4+}$ |
| Example compound No. 40 | C$_6$H$_5$ | 4-NO$_2$—C$_6$H$_4$ | CH$_3$ | Zn$^{2+}$ |
| Example compound No. 41 | C$_6$H$_5$ | 2-Cl—C$_6$H$_4$ | CH$_3$ | Zn$^{2+}$ |
| Example compound No. 42 | C$_6$H$_5$ | 2,4-Cl$_2$—C$_6$H$_3$ | CH$_3$ | Zn$^{2+}$ |
| Example compound No. 43 | 3,4-Cl$_2$—C$_6$H$_3$ | 2,4-Cl$_2$—C$_6$H$_6$ | CH$_3$ | Zn$^{2+}$ |
| Example compound No. 44 | C$_6$H$_5$ | 2-Cl, 4-NO$_2$—C$_6$H$_4$ | CH$_3$ | Zn$^{2+}$ |
| Example compound No. 45 | C$_6$H$_5$ | CF$_3$ | CH$_3$ | Zn$^{2+}$ |
| Example compound No. 46 | CF$_3$ | CH$_3$ | CH$_3$ | Zn$^{2+}$ |
| Example compound No. 47 | 4-CH$_3$—C$_6$H$_4$ | CH$_3$ | CH$_3$ | Zn$^{2+}$ |
| Example compound No. 48 | 4-CH$_3$—C$_6$H$_4$ | CCl$_3$ | CH$_3$ | Zn$^{2+}$ |
| Example compound No. 49 | 3,4-Cl$_2$—C$_6$H$_3$ | C$_6$H$_5$ | CH$_3$ | Ba$^{2+}$ |
| Example compound No. 50 | 3,4-Cl$_2$—C$_6$H$_3$ | C$_6$H$_5$ | CH$_3$ | Ti$^{4+}$ |

TABLE 2

|  | R$_1$ | R$_2$ | R$_3$ | Metal ion of salt |
|---|---|---|---|---|
| Example compound No. 51 | 3,4-Cl$_2$—C$_6$H$_3$ | C$_6$H$_5$ | CH$_3$ | Fe$^{2+}$ |
| Example compound No. 52 | 3,4-Cl$_2$—C$_6$H$_3$ | C$_6$H$_5$ | CH$_3$ | V(O)$^{2+}$ |
| Example compound No. 53 | 3,4-Cl$_2$—C$_6$H$_3$ | C$_6$H$_5$ | CH$_3$ | Zr(O)$^{2+}$ |
| Example compound No. 54 | C$_6$H$_5$ | 4-Cl—C$_6$H$_4$ | CH$_3$ | Al$^{3+}$ |
| Example compound No. 55 | C$_6$H$_5$ | 4-CH$_3$—C$_6$H$_4$ | CH$_3$ | Zn$^{2+}$ |
| Example compound No. 56 | C$_6$H$_5$ | 4-CH$_3$—C$_6$H$_4$ | CH$_3$ | Al$^{3+}$ |
| Example compound No. 57 | C$_6$H$_5$ | 4-CH$_3$—C$_6$H$_4$ | CH$_3$ | Zr$^{4+}$ |
| Example compound No. 58 | C$_6$H$_5$ | 4-CH$_3$O—C$_6$H$_4$ | CH$_3$ | Zn$^{2+}$ |
| Example compound No. 59 | C$_6$H$_5$ | 4-CH$_3$O—C$_6$H$_4$ | CH$_3$ | Al$^{3+}$ |
| Example compound No. 60 | C$_6$H$_5$ | 4-CH$_3$O—C$_6$H$_4$ | CH$_3$ | Zr$^{4+}$ |
| Example compound No. 61 | 3,4-Cl$_2$—C$_6$H$_3$ | 4-Cl—C$_6$H$_4$ | CH$_3$ | Ba$^{2+}$ |
| Example compound No. 62 | 3,4-Cl$_2$—C$_6$H$_3$ | 4-Cl—C$_6$H$_4$ | CH$_3$ | Ca$^{2+}$ |
| Example compound No. 63 | 3,4-Cl$_2$—C$_6$H$_3$ | 4-Cl—C$_6$H$_4$ | CH$_3$ | Zr(O)$^{2+}$ |
| Example compound No. 64 | 3,4-Cl$_2$—C$_6$H$_3$ | 4-Cl—C$_6$H$_4$ | CH$_3$ | V(O)$^{2+}$ |
| Example compound No. 65 | 3,4-Cl$_2$—C$_6$H$_3$ | 4-Cl—C$_6$H$_4$ | CH$_3$ | Fe$^{3+}$ |
| Example compound No. 66 | 3,4-Cl$_2$—C$_6$H$_3$ | 4-NO$_2$—C$_6$H$_4$ | CH$_3$ | — |
| Example compound No. 67 | 3,4-Cl$_2$—C$_6$H$_3$ | 4-NO$_2$—C$_6$H$_4$ | CH$_3$ | Zn$^{2+}$ |
| Example compound No. 68 | 3,4-Cl$_2$—C$_6$H$_3$ | 4-NO$_2$—C$_6$H$_4$ | CH$_3$ | Al$^{3+}$ |
| Example compound No. 69 | 3,4-Cl$_2$—C$_6$H$_3$ | 4-NO$_2$—C$_6$H$_4$ | CH$_3$ | Zr$^{4+}$ |
| Example compound No. 70 | 3,4-Cl$_2$—C$_6$H$_3$ | 2-Naphthyl | CH$_3$ | — |
| Example compound No. 71 | 3,4-Cl$_2$—C$_6$H$_3$ | 2-Naphthyl | CH$_3$ | Zn$^{2+}$ |
| Example compound No. 72 | 3,4-Cl$_2$—C$_6$H$_3$ | 2-Naphthyl | CH$_3$ | Al$^{3+}$ |
| Example compound No. 73 | 3,4-Cl$_2$—C$_6$H$_3$ | 2-Naphthyl | CH$_3$ | Zr$^{4+}$ |

TABLE 2-continued

| | R$_1$ | R$_2$ | R$_3$ | Metal ion of salt |
|---|---|---|---|---|
| Example compound No. 74 | 3,4-Cl$_2$—C$_6$H$_3$ | 2-Cl—C$_6$H$_4$ | CH$_3$ | — |
| Example compound No. 75 | 3,4-Cl$_2$—C$_6$H$_3$ | 2-Cl—C$_6$H$_4$ | CH$_3$ | Ba$^{2+}$ |
| Example compound No. 76 | 3,4-Cl$_2$—C$_6$H$_3$ | 3-Cl—C$_6$H$_4$ | CH$_3$ | — |
| Example compound No. 77 | 3,4-Cl$_2$—C$_6$H$_3$ | 3-Cl—C$_6$H$_4$ | CH$_3$ | Ba$^{2+}$ |
| Example compound No. 78 | 4-CH$_3$—C$_6$H$_4$ | C$_6$H$_5$ | CH$_3$ | — |
| Example compound No. 79 | 4-CH$_3$—C$_6$H$_4$ | C$_6$H$_5$ | CH$_3$ | Zn$^{2+}$ |
| Example compound No. 80 | 4-CH$_3$O—C$_6$H$_4$ | C$_6$H$_5$ | CH$_3$ | — |
| Example compound No. 81 | 4-CH$_3$O—C$_6$H$_4$ | C$_6$H$_5$ | CH$_3$ | Zn$^{2+}$ |
| Example compound No. 82 | 4-CH$_3$—C$_6$H$_4$ | 4-Cl—C$_6$H$_4$ | CH$_3$ | — |
| Example compound No. 83 | 4-CH$_3$—C$_6$H$_4$ | 4-Cl—C$_6$H$_4$ | CH$_3$ | Zn$^{2+}$ |
| Example compound No. 84 | 4-CH$_3$O—C$_6$H$_4$ | 4-Cl—C$_6$H$_4$ | CH$_3$ | — |
| Example compound No. 85 | 4-CH$_3$O—C$_6$H$_4$ | 4-Cl—C$_6$H$_4$ | CH$_3$ | Zn$^{2+}$ |
| Example compound No. 86 | 4-CH$_3$—C$_6$H$_4$ | 4-CH$_3$—C$_6$H$_4$ | CH$_3$ | — |
| Example compound No. 87 | 4-CH$_3$—C$_6$H$_4$ | 4-CH$_3$—C$_6$H$_4$ | CH$_3$ | Zn$^{2+}$ |
| Example compound No. 88 | 4-CH$_3$O—C$_6$H$_4$ | 4-CH$_3$—C$_6$H$_4$ | CH$_3$ | — |
| Example compound No. 89 | 4-CH$_3$O—C$_6$H$_4$ | 4-CH$_3$—C$_6$H$_4$ | CH$_3$ | Zn$^{2+}$ |
| Example compound No. 90 | 3,4-Cl$_2$—C$_6$H$_3$ | 3-Pyridyl | CH$_3$ | — |
| Example compound No. 91 | 3,4-Cl$_2$—C$_6$H$_3$ | 3-Pyridyl | CH$_3$ | Zn$^{2+}$ |
| Example compound No. 92 | 3,4-Cl$_2$—C$_6$H$_3$ | 4-Pyridyl | CH$_3$ | — |
| Example compound No. 93 | 3,4-Cl$_2$—C$_6$H$_3$ | 4-Pyridyl | CH$_3$ | Zn$^{2+}$ |
| Example compound No. 94 | 3,4-Cl$_2$—C$_6$H$_3$ | 2-Thenoyl | CH$_3$ | — |
| Example compound No. 95 | 3,4-Cl$_2$—C$_6$H$_3$ | 2-Thenoyl | CH$_3$ | Zn$^{2+}$ |

A pyrazolone derivative or a salt of the derivative used as a charge control agent according to the present invention is excellent in charge control characteristics, resistance to environment, and durability. Even when the concentration of a charge control agent including the pyrazolone derivative or the salt of the derivative according to the present invention as an active ingredient is low, i.e., not more than 1.0% by mass, the charge control agent can give a significantly large charge amount in the case where it is used for a toner. Therefore, when forming an electrostatic latent image, it is possible to obtain an image having no fog and favorable image concentration, dot reproducibility and fine line reproducibility.

In the present invention, it is preferable to use a charge control agent that is a pyrazolone derivative or a salt of the derivative after adjusting the volume average particle size thereof within the range of 0.1 to 20 µm and particularly preferably within the range of 0.1 to 10 µm. In the case where the volume average particle size is less than 0.1 µm, the amount of the charge control agent appearing on the surface of a toner becomes extremely less, and a desired charge control effect cannot be obtained. Meanwhile, in the case where the volume average particle size is more than 20 µm, the amount of the charge control agent that drops out of the toner is increased, and adverse effects such as in-machine contamination occur, which is not preferable.

Further, it is preferable to use a charge control agent that is a pyrazolone derivative or a salt of the derivative according to the present invention after adjusting the volume average particle size thereof to not more than 1.0 µm and particularly preferably within the range of 0.01 to 1.0 µm, in the case where it is used for a polymerized toner. In the case where the volume average particle size is more than 1.0 µm, the particle size distribution of the finally obtained toner for electrophotography becomes wider, and free particles are generated, which may cause reduction in performance and reliability. Meanwhile, in the case where the average particle size is within the above-mentioned range, it is advantageous in that the above-mentioned disadvantages do not occur, uneven distribution between toners is reduced, the dispersion in the toner becomes favorable, and variations in performance and reliability are reduced.

Examples of the method of causing a toner to include the pyrazolone derivative represented by the general formula (1) or the salt of the derivative, which is a charge control agent used in the present invention, include a method of adding it to the inside of toner particles in advance (internal addition) and a method of producing toner particles in advance and adding it to the surfaces of the toner particles (external addition). The method of adding it to the inside of toner particles in advance (internal addition) includes, for example, a method of adding it to binder resin together with a coloring agent, and kneading and pulverize them (pulverized toner) and a method of adding the pyrazolone derivative represented by the general formula (1) or the salt of the derivative to polymerizable monomer and polymerizing them to obtain a toner (polymerized toner).

The preferable additive amount in the case of internally adding the pyrazolone derivative represented by the general formula (1) or the salt of the derivative, which is a charge control agent used in the present invention, to toner particles, is 0.1 to 10 parts by mass and more preferably 0.2 to 5 parts by mass with respect to 100 parts by mass of binder resin.

In the case of externally adding the pyrazolone derivative represented by the general formula (1) or the salt of the derivative, which is a charge control agent used in the present invention, to toner particles, the additive amount is preferably 0.01 to 5 parts by mass and more preferably 0.01 to 2 parts by mass with respect to 100 parts by mass of binder resin. Further, it is preferable to cause it to mechanochemically adhere to the surfaces of toner particles.

Further, in the present invention, a charge control agent including the pyrazolone derivative represented by the general formula (1) or the salt of the derivative as an active ingredient can be used in combination with other known negatively charged charge control agents. Examples of the charge control agent to be used in combination include an azo-based iron complex or complex salt, an azo-based chromium complex or complex salt, an azo-based manganese complex or complex salt, an azo-based cobalt complex or complex salt, an azo-based zirconium complex or complex salt, a chromium complex or complex salt of a carboxylic acid derivative, a zinc complex or complex salt of a carboxylic acid derivative, an aluminum complex or complex salt of a carboxylic acid derivative, and a zirconium complex or complex salt of a carboxylic acid derivative. The carboxylic acid derivative is preferably an aromatic hydroxycarboxylic acid and more preferably a 3,5-di-tert-butylsalicylic acid. Other examples include a boron complex or complex salt, and a negatively charged resin-type charge control agent.

In the present invention, in the case of using the charge control agent and another charge control agent in combination, the additive amount of a charge control agent other than the charge control agent that is a pyrazolone derivative or a salt of the derivative is preferably 0.1 to 10 parts by mass with respect to 100 parts by mass of binder resin.

As the binder resin used for the toner according to the present invention, any kind of well-known binder resin can be used. Examples of the binder resin include vinyl polymers such as a styrene-based monomer, an acrylate-based monomer, and a methacrylate-based monomer, a copolymer including two or more kinds of these monomers, a polyester polymer, polyol resin, phenol resin, silicone resin, polyurethane resin, polyamide resin, furan resin, epoxy resin, xylene resin, terpene resin, coumarone indene resin, polycarbonate resin, and petroleum-based resin.

Examples of the styrene-based monomer, acrylate-based monomer, or methacrylate-based monomer, which forms the vinyl polymer or copolymer, include but not limited to the following.

Examples of the styrene-based monomer include styrene or derivatives thereof, such as styrene, o-methylstyrene, m-methylstyrene, p-methylstyrene, p-phenylstyrene, p-ethylstyrene, 2,4-dimethyl styrene, p-n-amyl styrene, p-tert-butyl styrene, p-n-hexyl styrene, p-n-octylstyrene, p-n-nonyl styrene, p-n-decylstyrene, p-n-dodecyl styrene, p-methoxystyrene, p-chlorostyrene, 3,4-dichlorostyrene, m-nitrostyrene, o-nitrostyrene, and p-nitrostyrene.

Examples of the acrylate-based monomer include an acrylic acid and esters thereof, such as an acrylic acid, a methyl acrylate, an ethyl acrylate, a propyl acrylate, an n-butyl acrylate, an isobutyl acrylate, an n-octyl acrylate, an n-dodecyl acrylate, a 2-ethylhexyl acrylate, a stearyl acrylate, a 2-chloroethyl acrylate, and a phenyl acrylate.

Examples of the methacrylate-based monomer include a methacrylic acid or esters thereof, such as a methacrylic acid, a methyl methacrylate, an ethyl methacrylate, a propyl methacrylate, an n-butyl methacrylate, an isobutyl methacrylate, an n-octyl methacrylate, an n-dodecyl methacrylate, a 2-ethylhexyl methacrylate, a stearyl methacrylate, a phenyl methacrylate, a dimethylaminoethyl methacrylate, and a diethylaminoethyl methacrylate.

Examples of other monomers, which form the vinyl polymer or copolymers include the following (1) to (18): (1) monoolefins such as ethylene, propylene, butylene, and isobutylene; (2) polyenes such as butadiene and isoprene; (3) vinyl halides such as vinyl chloride, vinylidene chloride, vinyl bromide, and vinyl fluoride; (4) vinyl esters such as vinyl acetate, vinyl propionate, and vinyl benzoate; (5) vinyl ethers such as vinyl methyl ether, vinyl ethyl ether, and vinyl isobutyl ether; (6) vinyl ketones such as vinyl methyl ketone, vinyl hexyl ketone, and methyl isopropenyl ketone; (7) N-vinyl compounds such as N-vinyl pyrrole, N-vinylcarbazole, N-vinylindole, and N-vinylpyrrolidone; (8) vinyl naphthalenes; (9) an acrylic acid or methacrylic acid derivative such as acrylonitrile, methacrylonitrile, and acrylamide; (10) unsaturated dibasic acids such as a maleic acid, a citraconic acid, an itaconic acid, an alkenylsuccinic acid, a fumaric acid, and a mesaconic acid; (11) unsaturated dibasic acid anhydride such as maleic anhydride, citraconic anhydride, and alkenylsuccinic anhydride; (12) monoesters of unsaturated dibasic acids such as maleic acid monomethyl ester, maleic acid monoethyl ester, maleic acid monobutyl ester, citraconic acid monomethyl ester, citraconic acid monoethyl ester, citraconic acid monobutyl ester, itaconic acid monomethyl ester, alkenylsuccinic acid monomethyl ester, fumaric acid monomethyl ester, and mesaconic acid monomethyl ester; (13) dimethyl maleic acid, and unsaturated dibasic acid esters such as dimethyl fumaric acid; (14) $\alpha,\beta$-unsaturated acid anhydride such as a crotonic acid, and $\alpha,\beta$-unsaturated acids such as a cinnamic acid; (15) crotonic anhydride, and cinnamic acid anhydride; (16) monomers having a carboxyl group such as anhydride of the $\alpha,\beta$-unsaturated acid and a lower fatty acid and acid anhydrides of an alkenyl malonic acid, an alkenyl glutaric acid, and an alkenyl adipic acid and monoesters of anhydride and acid anhydrides; (17) acrylic acids or methacrylic acid hydroxyalkyl esters such as 2-hydroxyethyl acrylate, 2-hydroxyethyl methacrylate, and 2-hydroxypropyl methacrylate; and (18) monomers having a hydroxy group such as 4-(1-hydroxy-1-methylbutyl) styrene, and 4-(1-hydroxy-1-methylhexyl) styrene.

In the toner according to the present invention, the vinyl polymer or copolymer of the binder resin may have a cross-linked structure crosslinked with a cross-linking agent having two or more vinyl groups. Examples of the cross-linking agent used in this case include divinylbenzene and divinyl naphthalene as an aromatic divinyl compound. Example of the diacrylate compounds connected with alkyl chains include ethylene glycol diacrylate, 1,3-butylene glycol diacrylate, 1,4-butanediol diacrylate, 1,5-pentanediol diacrylate, 1,6-hexanediol diacrylate, neopentyl glycol diacrylate, and those in which methacrylate is substituted with acrylate of the above-mentioned compound.

Examples of diacrylate compounds connected with alkyl chains including an ether bond include diethylene glycol diacrylate, triethylene glycol diacrylate, tetraethylene glycol diacrylate, polyethylene glycol #400 diacrylate, polyethylene glycol #600 diacrylate, dipropylene glycol diacrylate, and a compound in which acrylate of the above-mentioned compound is substituted with methacrylate.

Other examples include a diacrylate compound connected with a chain including at least one of an aromatic group and an ether bond, and dimethacrylate compounds. Examples of the polyester type diacrylates include a product name MANDA (manufactured by Nippon Kayaku Co., Ltd.).

Examples of the polyfunctional crosslinking agent include pentaerythritol triacrylate, trimethylol ethane triacrylate, trimethylolpropane triacrylate, tetramethylolmethane tetraacrylate, oligoester acrylate, those in which acrylate of the above-mentioned compounds is substituted with methacrylate, triallyl cyanurate, and triallyl trimellitate.

These cross-linking agents can be used preferably in an amount of 0.01 to 10 parts by mass with respect to 100 parts by mass of other monomer components, and particularly preferably in an amount of 0.03 to 5 parts by mass. Among these cross-linkable monomers, those suitably used for toner resin in terms of fixability and offset resistance include an aromatic divinyl compound (particularly, divinylbenzen is preferable), diacrylate compounds connected with a linkage chain including an aromatic group and an ether bond. Among these, combinations of monomers from which a styrene-based copolymer or a styrene-acrylate-based copolymer is obtained are preferable.

In the case where the binder resin is styrene-acrylate-based resin, in the molecular weight distribution of the resin component being soluble in tetrahydrofuran (hereinafter, referred to as THF) measured by gel permeation chromatography (hereinafter, referred to as GPC), resin having at least one peak in the region of molecular weight of 3,000 to 50,000 (the converted number average molecular weight) and at least one peak in the region of molecular weight of not less than 100,000 is preferable in terms of the fixability, offset property, and storage stability. Further, also binder resin in which the THF-soluble components having the molecular weight of not more than 100,000 occupy 50 to 90% is preferable. More preferably, those having a main peak in the region of molecular weight of 5,000 to 30,000, most preferably 5,000 to 20,000.

In the case where the binder resin is a vinyl polymer such as styrene-acrylate-based resin, the acid value is preferably 0.1 mgKOH/g to 100 mgKOH/g, more preferably 0.1 mgKOH/g to 70 mgKOH/g, and even more preferably 0.1 mgKOH/g to 50 mgKOH/g.

Examples of the monomer forming the polyester-based polymer include the following.

Examples of the divalent alcohol component include ethylene glycol, propylene glycol, 1,3-butanediol, 1,4-butanediol, 2,3-butanediol, diethylene glycol, triethylene glycol, 1,5-pentanediol, 1,6-hexanediol, neopentyl glycol, 2-ethyl-1,3-hexanediol, hydrogenated bisphenol A, and diol obtained by polymerizing bisphenol A with a cyclic ether such as ethylene oxide and propylene oxide.

In order to crosslink the polyester resin, it is preferable to use the trivalent or higher-valent alcohol in combination. Examples of the trivalent or higher polyvalent alcohol include sorbitol, 1,2,3,6-hexane tetrol, 1,4-sorbitan, pentaerythritol, dipentaerythritol, tripentaerythritol, 1,2,4-butanetriol, 1,2,5-pentatriol, glycerol, 2-methylpropane triol, 2-methyl-1,2,4-butanetriol, trimethylol ethane, trimethylolpropane, and 1,3,5-trihydroxybenzene.

Examples of the acid component forming the polyester-based polymer include benzene dicarboxylic acids such as a phthalic acid, an isophthalic acid, and a terephthalic acid, or anhydride thereof, alkyl dicarboxylic acids such as a succinic acid, an adipic acid, a sebacic acid, and an azelaic acid, or anhydride thereof, unsaturated dibasic acids such as a maleic acid, a citraconic acid, an itaconic acid, an alkenyl-succinic acid, a fumaric acid, a mesaconic acid, and unsaturated dibasic acid anhydride such as maleic anhydride, citraconic anhydride, itaconic anhydride, and alkenylsuccinic anhydride. Further, examples of the trivalent or higher polyvalent carboxylic acid component include a trimellitic acid, a pyromellitic acid, a 2,5,7-naphthalene tricarboxylic acid, a 1,2,4-naphthalene tricarboxylic acid, a 1,2,4-butanetricarboxylic acid, a 1,2,5-hexanetricarboxylic acid, 1,3-dicarboxy-2-methyl-2-methylene carboxypropane, tetra (methylene carboxy) methane, a 1,2,7,8-octane tetracarboxylic acid, an empol trimer acid, and anhydride thereof, and partial lower alkyl ester.

In the case where the binder resin is polyester-based resin, it is preferable that there is at least one peak in the region of molecular weight of 3,000 to 50,000 in the molecular weight distribution of the THF soluble component of the resin component in terms of the fixability and offset resistance of the toner. In addition, the binder resin in which the THF-soluble components having the molecular weight of not more than 100,000 occupy 60 to 100% is also preferable. It is more preferable that there is at least one peak in the region of molecular weight of 5,000 to 20,000. In the present invention, the molecular weight distribution of the binder resin is measured by GPC using the TFF as a solvent.

In the present invention, two or more kinds of amorphous polyester resin and crystalline polyester resin may be mixed and used. In this case, it is preferable to select materials taking into account the compatibility. As the amorphous polyester resin, those synthesized from a polyvalent carboxylic acid component, preferably from an aromatic polyvalent carboxylic acid and a polyhydric alcohol component, are suitably used. As the crystalline polyester resin, those synthesized from a divalent carboxylic acid component, preferably from an aliphatic dicarboxylic acid and a dihydric alcohol component, are suitably used.

As the binder resin that can be used for the toner according to the present invention, among the vinyl polymer component and/or the polyester-based resin component, resin containing a monomer component capable of reacting with both of the former resin components, can also be used. Among monomers forming the polyester-based resin component, examples of those reactive with the vinyl polymer include unsaturated dicarboxylic acids such as a phthalic acid, a maleic acid, a citraconic acid, and an itaconic acid, and anhydride thereof. Examples of the monomer forming the vinyl polymer component include those having a carboxyl group or a hydroxyl group, and an acrylic and methacrylic acid esters. Further, in the case of using the polyester-based polymer, the vinyl polymer, and other binder resin in combination, it is preferable that the resin having the acid value of 0.1 to 50 mgKOH/g includes 60% by mass or more of all of the binder resin.

In the present invention, the acid value of the binder resin component of the toner composition is obtained by the following method, and the basic operation is in accordance with JIS K-0070.

(1) A sample from which additives other than binder resin (polymer component) are removed in advance is used. Alternatively, the acid value and the content of components other than the binder resin and crosslinked binder resin are obtained in advance. 0.5 to 2.0 g of the pulverized sample is accurately weighed, and the weight of the polymer component is defined as Wg. In the case where the acid value of the binder resin is measured from a toner, for example, the acid value and content of a coloring agent, a magnetic material, or the like are separately measured, and the acid value of the binder resin is obtained by calculation.

(2) Place the sample in a beaker of 300 (ml), and dissolve the sample by adding 150 (ml) of a mixed solution of toluene/ethanol (volume ratio 4/1).

(3) Titrate with a 0.1 mol/L KOH ethanol solution by using a potentiometric titrator.

(4) The use amount of the KOH solution at this time is defined as S (ml). Blank is measured at the same time with the use amount of the KOH solution at this time defined as B (ml). Calculation is performed by the following formula (1). Note that f represents the factor of the KOH concentration.

$$\text{Acid value (mgKOH/g)}=[(S-B)\times f\times 5.61]/W \qquad (1)$$

The binder resin and composition including binder resin of a toner have a glass transition temperature ($T_g$) of preferably 35 to 80° C., particularly favorably 40 to 75° C., from the viewpoint of the toner storage stability. In the case where $T_g$ is lower than 35° C., the toner is likely to be deteriorated under a high-temperature atmosphere, and an offset easily occurs at the time of fixing. Further, in the case where $T_g$ exceeds 80° C., the fixability is likely to be reduced. In the polymerized toner according to the present invention, binder resin having a softening point in the range of 80 to 140° C. is suitably used.

In the case where the softening point of the binder resin is less than 80° C., the toner after fixing and during storage and the image stability of the toner are deteriorated in some cases. Meanwhile, in the case where the softening point exceeds 140° C., the low temperature fixability is deteriorated in some cases.

The magnetic material that can be used in the present invention is not particularly limited, and any of well-known magnetic material can be used. For example, (1) magnetic iron oxides such as magnetite, maghemite, ferrite, and iron oxides including another metal oxide, or (2) metals such as iron, cobalt, and nickel, and alloys of these metals and metals such as aluminum, cobalt, copper, lead, magnesium, tin, zinc, antimony, beryllium, bismuth, cadmium, calcium, manganese, selenium, titanium, tungsten, and vanadium, and (3) mixtures thereof are used.

The use amount of the magnetic material is 10 to 200 parts by mass, preferably 20 to 150 parts by mass, with respect to 100 parts by mass of binder resin. The number average particle size of these magnetic materials is preferably 0.1 to 2 μm and more preferably 0.1 to 0.5 μm. The number average particle size can be obtained by measuring the photograph enlarged by a transmission electron microscope with a digitizer or the like.

Further, it is preferable that the magnetic material has the coercive force of 20 to 150 oersted, the saturation magnetization of 50 to 200 emu/g, and the remanent magnetization of 2 to 20 emu/g as the magnetic properties under application of 10 K Oersted.

The magnetic material can be used also as a coloring agent. Examples of the coloring agent that can be used in the present invention include black or blue dyes or pigment particles in the case of a black toner. Examples of the black or blue pigment include carbon black, aniline black, acetylene black, phthalocyanine blue, and indanthrene blue. Examples of the black or blue dye include an azo-based dye, an anthraquinone-based dye, a xanthene-based dye, and a methine-based dye.

In the case where the coloring agent is used for a color toner, the coloring agent is not particularly limited, and any of well-known coloring agents can be used. As a magenta coloring agent, a condensed azo compound, a diketopyrrolopyrrole compound, an anthraquinone compound, a quinacridone compound, basic dyes, lake dyes, naphthol dyes, a benzimidazolone compound, a thioindigo compound, and a perylene compound are used. The above-mentioned pigment may be used alone. However, it is more preferable to use the dye and the pigment in combination to improve the sharpness from the viewpoint of the image quality of a full-color image.

As the cyan coloring agent, copper phthalocyanine compounds and derivatives thereof, anthraquinone, base dye lake compounds can be used.

As the yellow coloring agent, a condensed azo compound, an isoindolinone compound, an anthraquinone compound, an azo metal complex, a methine compound, and an allylamide compound are used.

The toner according to the present invention may be mixed with a carrier and used as a two-component developer. As the carrier used in the present invention, typical carriers such as ferrite and magnetite and resin-coated carriers can be used.

Further, a binder-type carrier core in which magnetic powder is dispersed in resin can also be used.

As a method of covering the surface of the carrier core with at least a resin coating agent in the resin-coated carrier, a method of dissolving or suspending resin in a solvent, coating the carrier core with the resin, and causing the resin coating agent to adhere to the carrier core, or a method of simply mixing in a powder state can be applied. The ratio of the resin coating agent to the resin-coated carrier may be appropriately determined. However, it is preferably from 0.01 to 5% by mass, more preferably 0.1 to 1% by mass, with respect to the resin-coated carrier.

Usage examples of coating the magnetic material with a coating agent of a mixture of two or more kinds include (1) those obtained by treating 100 parts by mass of titanium oxide fine powder with 12 parts by mass of a mixture of dimethyldichlorosilane and dimethyl silicon oil (mass ratio 1:5) (2) those obtained by treating 100 parts by mass of silica fine powder with 20 parts by mass of a mixture of dimethyldichlorosilane and dimethyl silicon oil (mass ratio 1:5).

In the above-mentioned resin, a styrene-methyl methacrylate copolymer, a mixture of fluorine-including resin and a styrene-based copolymer, or silicone resin is preferably used, and the silicon resin is particularly preferable.

Examples of the silicone resin include nitrogen-including silicone resin and modified silicone resin generated by the reaction of nitrogen-including silane coupling agent and silicone resin.

As the magnetic material of the carrier core, oxides such as ferrite, iron-excess-type ferrite, magnetite, and a γ-iron oxide, metals such as iron, cobalt, and nickel, and alloys thereof can be used. Preferable examples include copper-zinc-iron-based ferrite including copper, zinc, and iron components as main components, and manganese-magnesium-iron-based ferrite including manganese, magnesium, and iron components as main components.

The resistance value of the carrier is preferably adjusted to $10^6$ to $10^{10}$·Ω cm by adjusting the degree of irregularity on the surface of the carrier and the amount of the resin to be coated. A carrier having a particle size of 4 to 200 μm can be used. However, the particle size is preferably 10 to 150 μm, and more preferably 20 to 100 μm. In particular, the resin-coated carrier preferably has a median diameter of 20 to 70 μm.

It is preferable to use a two-component-based developer having 1 to 200 parts by mass of the toner according to the present invention with respect to 100 parts by mass of the carrier, and more preferably 2 to 50 parts by mass of with respect to 100 parts by mass of the carrier.

The toner according to the present invention may further include wax. The wax used in the present invention is not particularly limited. Examples of the wax include the following: aliphatic hydrocarbon wax such as low molecular weight polyethylene, low molecular weight polypropylene, polyolefin wax, microcrystalline wax, paraffin wax, and Sasol wax, oxides of aliphatic hydrocarbon wax such as oxidized polyethylene wax, block copolymers thereof, plant-based wax such as candelilla wax, carnauba wax, wood wax, and jojoba wax, animal-based wax such as bees wax, lanolin, and whale wax, mineral wax such as ozokerite, ceresin, and petrolatum, waxes including fatty acid ester as a main component such as montanic ester wax and castor wax, and those obtained by deoxidizing a part or all of fatty acid esters such as deoxidized carnauba wax.

The wax used in the present invention preferably has a melting point of 50 to 140° C., more preferably 70 to 120° C., in order to balance the fixability and the offset resistance. In the case where the melting point is less than 50° C., the blocking resistance is likely to be reduced. In the case where the melting point exceeds 140° C., the offset resistance effect becomes difficult to be expressed.

Further, by using two or more different types of wax in combination, the plasticizing action and releasing action, which are the action of the wax, can be simultaneously expressed.

Usage examples include a combination of two or more different waxes having a difference in melting point of 10° C. to 100° C. and a combination of polyolefin and graft-modified polyolefin.

In the case where two types of waxes are selected and the waxes have a similar structure, a wax having a relatively low melting point exerts a plasticizing action, and a wax having a relatively high melting point exerts a releasing action. At this time, in the case where the difference in melting point is from 10 to 100° C., the function separation is effectively expressed. In the case where the difference in melting point is less than 10° C., the function separation effect is difficult to be expressed. In the case where the difference in melting point exceeds 100° C., the function by interaction is difficult to be emphasized. In this case, the melting point of at least one of the waxes is preferably 70 to 120° C., more preferably 70 to 100° C., and the function separation effect is likely to be easily exerted.

In the toner according to the present invention, the total content of these waxes is preferably 0.2 to 20 parts by mass, more preferably 0.5 to 10 parts by mass, with respect to 100 parts by mass of binder resin.

A fluidity improver may be added to the toner according to the present invention. The fluidity improver is added to the surface of the toner to improve the fluidity of the toner (make it easy to flow). The fluidity improver is not particularly limited, and any of well-known fluidity improvers can be used. Fine powder silica, fine powder titanium oxide, or fine powder alumina is preferable, and silica obtained by surface-treating these with a silane coupling agent or silicone oil is more preferable. The particle size of the fluidity improver is preferably 0.001 to 2 µm as an average primary particle size, and more preferably 0.002 to 0.2 µm.

To the toner according to the present invention, as other additives, various types of metal soap, a fluorine-based surfactant, and dioctyl phthalate; a tin oxide, a zin oxide, carbon black, and an antimony oxide as conductivity imparting agents; and inorganic fine powder such as a titanium oxide, an aluminum oxide, and alumina can be added as necessary in order to, for example, protect a photoreceptor/carrier, improve the cleaning performance, adjust the thermal/electrical/physical characteristics, the resistance, and the softening point, and improve the fixing ratio. Further, these inorganic fine powders may be rendered hydrophobic as necessary. Further, lubricants such as polytetrafluoroethylene, zinc stearate, and polyvinylidene fluoride, abrasives such as a cesium oxide, a silicon carbide, and strontium titanate, an anti-caking agent, and white fine particles and black fine particles, which have opposite polarity to the toner particles, can be also used in small amounts as developability improver.

It is also preferable to treat these additives with treatment agents such as silicone varnish, various modified silicone varnish, silicone oil, various modified silicone oil, a silane coupling agent, a silane coupling agent having a functional group, and other organosilicon compounds, or various treatment agents for the purpose of charge quantity control or the like.

In the present invention, a desired toner for electrostatic charge development can also be obtained by thoroughly mixing and stirring a charge control agent with the above-mentioned additive and a toner by a mixer such as a Henschel mixer, a ball mill, a Nauta mixer, a V-type mixer, a W-type mixer, and a super mixer to externally add them to the surfaces of toner particles uniformly.

The toner according to the present invention is thermally stable, that there is no thermal change during the electrophotography process, and is capable of maintaining stable charging characteristics. Further, since it is uniformly dispersed in any binder resin, the charge distribution of a fresh toner is very uniform. Therefore, even in the untransferred and recovered toner (waste toner) in the present invention, almost no change in the saturated triboelectric charge quantity and charge distribution is recognized as compared with a fresh toner.

As a method of producing the toner according to the present invention, it can be produced by a known production method. Preferable examples of the production method include a method of thoroughly mixing the above-mentioned toner-forming materials such as binder resin, a charge control agent and a coloring agent by a mixer such as a ball mill, thoroughly kneading the mixture by a heating kneading apparatus such as a heat roll kneader, cooling and solidifying, pulverizing, and then classifying it to obtain a toner (pulverization method).

Further, it can be produced also by a method in which the above-mentioned mixture is dissolved in a solvent, atomized by spraying, dried, and classified to obtain a toner. Further, it can be produced also by a toner production method using a polymerization method of mixing the monomer that forms binder resin with a predetermined material to prepare an emulsion or suspension, and then, polymerizing it to obtain a toner, or a method of causing a core material and a shell material in a so-called microcapsule toner, which has one or both of the core material and the shell material, to include a predetermined material. Further, if necessary, the toner according to the present invention can be produced by thoroughly mixing a desired additive and toner particles by a mixer such as a Henschel mixer.

The method of producing the toner according to the present invention by the above-mentioned pulverization method will be described in more detail. First, binder resin, a coloring agent, a charge control agent, and other necessary additives are uniformly mixed. The mixing can be performed using a known stirrer such as a Henschel mixer, a super mixer, and a ball mill. The obtained mixture is thermally melt-kneaded using a closed-type kneader or a single or twin screw extruder. The kneaded material is cooled before being coarsely pulverized using a crusher or a hammer mill, and finely pulverized by a pulverizer such as a jet mill and a high-speed rotor rotary mill. Further, classification is performed to obtain a predetermined particle size using an air classifier such as an elbow jet of an inertial classification system using the Coanda effect, and a microplex of a cyclone (centrifugal) classification system, and a DS separator. Further, in the case of treating the surface of the toner with an external additive or the like, the toner and the external additives are stirred and mixed by a high-speed stirrer such as a Henschel mixer and a super mixer.

Further, the toner according to the present invention can be produced also by a suspension polymerization method or an emulsion polymerization method. In the suspension polymerization method, a polymerizable monomer, a coloring agent, a polymerization initiator, a charge control agent, and, if necessary, a cross-linking agent and other additives are uniformly dissolved or dispersed to prepare a monomer composition. After that, it is dispersed in a continuous phase including this monomer composition and a dispersion stabilizer, e.g., in an aqueous phase, using an appropriate stirrer or disperser such as a homomixer, a homogenizer, an atomizer, a microfluidizer, a one-liquid fluid nozzle, a gas-liquid fluid nozzle, an electrical emulsifier. It is preferable that the stirring speed, temperature, and time are adjusted and granulation is performed so that the droplets of the polymerizable monomer composition have a desired toner particle size. The polymerization reaction is simultaneously performed at 40 to 90° C., and toner particles having a desired particle size can be obtained. The obtained toner particles are washed, filtered off, and then, dried. As the external addition treatment after producing the toner particles, the above-mentioned method can be used.

In the case of production by the emulsion polymerization method, it is more excellent in uniformity than the particles obtained by the suspension polymerization method described above. However, since the average particle size is as extremely small as 0.1 to 1.0 it can be produced by so-called seed polymerization in which the polymerizable monomer is post-added with the emulsified particles as the nucleus to grow the particles or a method of coalescing and fusing the emulsified particles to obtain appropriate average particle size in some cases.

In the production by these polymerization methods, it is unnecessary to impart brittleness to the toner particles since it does not undergo a pulverization step, and a large amount of low softening point substances that have been difficult to use in the existing pulverization method can be used, which makes it possible to broaden the selection range of materials. The releasing agent or coloring agent, which is a hydrophobic material, is unlikely to be exposed on the surfaces of the toner particles, so that contamination of on the toner carrying member, the photoreceptor, the transfer roller, and the fuser can be reduced.

By producing the toner according to the present invention by a polymerization method, it is possible to further improve the characteristics such as image reproducibility, transferability, and color reproducibility, reduce the particle size of the toner to cope with minute dots, and relatively easily obtain a toner having sharp particle distribution.

As the polymerizable monomer to be used for producing the toner according to the present invention by a polymerization method, a radical-polymerizable vinyl-based polymerizable monomer is used. As the vinyl-based polymerizable monomer, a monofunctional polymerizable monomer or polyfunctional polymerizable monomer can be used.

Examples of the water-soluble initiator to be used for producing the toner according to the present invention by a polymerization method include ammonium persulfate, potassium persulfate, 2,2'-azobis (N, N'-dimethyleneisobutyroamidine)hydrochloride, 2,2'-azobis(2-amidinopropane) hydrochloride, azobis (isobutylamidine) hydrochloride, sodium 2,2'-azobisisobutyronitrile sulfonate, ferrous sulphate, and hydrogen peroxide.

The additive amount of the polymerization initiator is preferably 0.5 to 20 parts by mass with respect to 100 parts by mass of the polymerizable monomer, and the polymerization initiator may be used alone or in combination. Examples of the dispersant to be used for producing a polymerized toner include tricalcium phosphate, magnesium phosphate, aluminum phosphate, zinc phosphate, calcium carbonate, magnesium carbonate, aluminum hydroxide, calcium metasilicate, calcium sulfate, barium sulfate, bentonite, silica, and alumina, as the inorganic oxide. As the organic compound, polyvinyl alcohol, gelatin, methylcellulose, methyl hydroxypropyl cellulose, ethyl cellulose, sodium salt of carboxymethyl cellulose, starch, and the like are used. It is preferable to use 0.2 to 2.0 parts by mass of these dispersants with respect to 100 parts by mass of the polymerizable monomer.

As these dispersants, commercially available dispersants may be used as they are. Alternatively, in order to obtain dispersed particles having a fine uniform particle size, the inorganic compound may be produced in a dispersion medium under high-speed stirring.

Since the toner obtained by the above-mentioned polymerization method tends to have a smaller degree of irregularity of toner particles than the toner obtained by the pulverization method without special treatment, and has an irregular shape, the contact area between the electrostatic latent image carrier and the toner is increased, which improves the toner adhesion. As a result, there is less in-machine contamination, and an image with a higher image density and higher quality can be easily obtained.

Further, as for the toner by the pulverization method, there is a method for reducing the degree of irregularity on the surface of the toner such as a hot water bath method dispersing toner particles in water and heating them, a heat treatment method of causing toner particles to pass through a hot air flow, and a mechanical impact method of applying mechanical energy to toner particles for treatment. Examples of the apparatus effective for reducing the degree of irregularity include a mechano-fusion system (manufactured by Hosokawa Micron Co., Ltd) that applies a dry mechanochemical method, an I-type jet mill, a hybridizer (manufactured by Nara Machinery Co., Ltd) that is a mixing apparatus including a rotor and a liner, and a Henschel mixer that is a mixer including a high speed stirring blade.

The toner according to the present invention can be used in a one-component developing method that is one of image forming methods. The one-component developing method is a method in which a thinned toner is supplied to a latent image carrier to develop a latent image. The thinning of the toner is usually performed using an apparatus including a toner transporting member, a toner layer thickness regulating member, and a toner supply auxiliary member, in which the toner supply auxiliary member and the toner transporting member, and the toner layer thickness regulating member and the toner transporting member are in contact with each other.

A case where the toner according to the present invention is applied to a two-component developing method will be specifically described. The two-component developing method is a method of using a toner and a carrier (one having a role as a charge-imparting material and a toner transporting material), and the above-mentioned magnetic material or glass beads are used as the carrier. The developer (toner and carrier) is stirred by a stirring member to generate a predetermined amount of charges, and transported to a development site by a magnet roller or the like. The developer is held on the surface of the magnet roller by a magnetic force to form a magnetic brush regulated in the thickness of layers to an appropriate height by a developer regulating plate or the like. As a developing roller rotates, the developer moves on the roller and comes into contact with the electrostatic latent image carrier or is opposed to the electrostatic latent image carrier at regular intervals in a non-contact state, which makes a latent image developed and visualized. In the case of development in the non-contact state, normally, a driving force for the toner to fly over the space of a constant interval by generating a direct current electric field between the developer and the latent image carrier. However, it can also be applied to a method of superimposing alternate current in order to develop an image to obtain a sharper image.

Further, the charge control agent used in the present invention is suitable also as a charge control agent (charge enhancer) in electrostatic powder coating paint. Specifically, this electrostatic coating paint using a charge enhancer is excellent in resistance to environment, storage stability, and, particularly, thermal stability and durability, the coating efficiency thereof reaches 100%, and a thick film free from coating film defects can be formed.

EXAMPLES

Hereinafter, the present invention will be described with reference to examples, but these examples do not limit the present invention. In the examples, "parts" all represent "parts by mass".

Analysis of the purity, composition ratio, and the like of a pyrazolone derivative represented by the general formula (1) or a salt of the derivative, which is used in the present invention, was performed by high performance liquid chromatography (hereinafter, abbreviated as HPLC). Purification of these compounds was performed by purification by column chromatography, adsorption purification with activated carbon, activated clay, and the like, recrystallization with a solvent, a crystallization method, or the like. Further, the compound was identified by NMR analysis. As the conditions of HPLC, the measurement was performed under the conditions that THF:methanol:water:TFA=450:400:150:2 as the developing solvent, Develosil ODS-HG-5 was used as the column, the flow rate was 1.0 ml/min, and the detection wavelength was 254 nm.

Synthesis of Charge Control Agent

The pyrazolone derivative represented by the general formula (1) or a salt of the derivative, which is used as a charge control agent according to the present invention, can be produced by performing a well-known substitution reaction or a metalation reaction following the well-known substitution reaction. Specific synthesis examples were performed as follows.

Synthesis Example 1 (Synthesis of Example Compound No. 1)

To a 500 mL four-necked flask that includes a stirrer, a cooling tube, and a thermometer, and is purged with nitrogen, 43.2 g (177.8 mmol) of 1-(dichlorophenyl)-3-methyl-5-pyrazolone which corresponds to that $R_1$ is a 3,4-dichlorophenyl group, and $R_3$ is a methyl group in the general formula (1), 300 ml of 1,4-dioxane, and 24.8 g (334.4 mmol) of calcium hydroxide were added. Into this, 25.0 g (177.8 mmol) of benzoyl chloride which corresponds to that $R_2$ is a phenyl group in the general formula (1) was dropped at room temperature. It was heated to 95° C., and stirred under reflux for 2 hours. After allowing it to cool to room temperature, the reaction solution was added to 1,000 ml of 2N aqueous hydrochloric acid and stirred for 1 hour, and then, the precipitated crude crystals were collected by filtration. The obtained crude crystals were dispersed and washed twice with methanol, followed by dispersion washing with ion exchanged water three times. After that, it was dried under reduced pressure overnight at 80° C. to obtain 59.5 g (yield 96.3%) of ocher crystals.

The structure of the obtained ocher crystals was identified using NMR. As a result, the following 11 hydrogen signals were detected by 1H-NMR (CDCl$_3$). δ(ppm)=2.09 (3H), 7.48-7.54 (3H), 7.61 (1H), 7.64 (2H), 7.85 (1H), and 8.11 (1H). It was found that a pyrazolone derivative in which $R_1$ was a dichlorophenyl group, $R_2$ was a phenyl group, and $R_3$ was a methyl group in the general formula (1) was obtained. Further, as a result of HPLC analysis, the purity thereof was 98.0% with the peak area ratio.

Synthesis Example 2 (Synthesis of Example Compound No. 2)

To a 500 mL four-necked flask that includes a stirrer, a cooling tube, and a thermometer, 13.9 g (40 mmol) of the compound of the synthesis example 1 which corresponds to that $R_1$ is a 3,4-dichlorophenyl group, $R_2$ is a phenyl group, and $R_3$ is a methyl group in the general formula (1), and 400 ml of methanol were added, and the pH thereof was adjusted to pH7 with 6N aqueous ammonia. Into this, 5.7 g (20 mmol) of zinc sulfate dissolved in water was dropped at room temperature. It was heated to 40° C., and stirred for 4 hours. After allowing it to cool to room temperature, the precipitated crude crystals were collected by filtration. The obtained crude crystals were dispersed and washed once with methanol, followed by dispersion washing once with ion exchanged water. The obtained crystals were dried under reduced pressure overnight at 80° C. to obtain 14.9 g (yield 98.5%) of yellowish-white crystals.

The structure of the obtained yellowish-white crystals was identified using NMR. As a result, the following 22 hydrogen signals were detected by 1H-NMR (DMSO-d$_6$). δ(ppm)= 1.61 (6H), 7.39 (4H), 7.44 (4H), 7.48 (2H), 7.50 (2H), 7.90 (2H), and 8.29 (2H). It was found that zinc salt of a pyrazolone derivative in which $R_1$ was a 3,4-dichlorophenyl group, $R_2$ was a phenyl group, and $R_3$ was a methyl group in the general formula (1) was obtained.

Synthesis Example 3 (Synthesis of Example Compound No. 3)

To a 1000 mL four-necked flask that includes a stirrer, a cooling tube, and a thermometer, 15.0 g (43 mmol) of the compound of the synthesis example 1 which corresponds to that $R_1$ is a 3,4-dichlorophenyl group, $R_2$ is a phenyl group, and $R_3$ is a methyl group in the general formula (1), and 700 ml of ethanol were added, and the pH thereof was adjusted to pH7 with 6N aqueous ammonia. Into this, 2.5 g (7.2 mmol) of aluminum sulfate heated and dissolved in water was dropped at room temperature. It was heated to 40° C., and stirred for 4 hours. After allowing it to cool to room temperature, the precipitated crude crystals were collected by filtration. The obtained crude crystals were dispersed and washed once with methanol, followed by dispersion washing once with ion exchanged water. The obtained crystals were dried under reduced pressure overnight at 80° C. to obtain 13.5 g (yield 87.9%) of skin-color crystals.

The structure of the obtained skin-color crystals was identified using NMR. As a result, the following 33 hydrogen signals were detected by 1H-NMR (CDCl$_3$). δ(ppm)= 1.88-1.95 (9H), 7.25-7.55 (18H), 7.71-7.82 (3H), and 8.08-8.18 (3H). It was found that aluminum salt of a pyrazolone derivative in which $R_1$ was a 3,4-dichlorophenyl group, $R_2$ was a phenyl group, and $R_3$ was a methyl group in the general formula (1) was obtained.

Synthesis Example 4 (Synthesis of Example Compound No. 4)

To a 1000 mL four-necked flask that includes a stirrer, a cooling tube, and a thermometer, 15.1 g (43 mmol) of the compound of the synthesis example 1 which corresponds to that $R_1$ is a 3,4-dichlorophenyl group, $R_2$ is a phenyl group, and $R_3$ is a methyl group in the general formula (1), and 750 ml of methanol were added, and the pH thereof was adjusted to pH7 with 6N aqueous ammonia. Into this, 2.6 g (10.8 mmol) of zirconium chloride dissolved in methanol was dropped at room temperature. It was stirred for 4 hours at room temperature. After that, the precipitated crude crystals were collected by filtration. The obtained crude crystals were dispersed and washed once with methanol, followed by dispersion washing once with ion exchanged water. The obtained crystals were dried under reduced pressure overnight at 80° C. to obtain 14.4 g (yield 89.6%) of ocher crystals.

The structure of the obtained ocher crystals was identified using NMR. As a result, the following 44 hydrogen signals were detected by 1H-NMR (CDCl$_3$). δ(ppm)=1.84 (12H), 7.01 (4H), 7.38-7.40 (16H), 7.55 (4H), 7.80 (4H), and 8.17 (4H). It was found that zirconium salt of a pyrazolone derivative in which $R_1$ was a 3,4-dichlorophenyl group, $R_2$ was a phenyl group, and $R_3$ was a methyl group in the general formula (1) was obtained.

Synthesis Example 5 (Synthesis of Example Compound No. 19)

To a 500 mL four-necked flask that includes a stirrer, a cooling tube, and a thermometer, and is purged with nitrogen, 24.4 g (140 mmol) of 1-phenyl-3-methyl-5-pyrazolone which corresponds to that $R_1$ is a phenyl group and $R_3$ is a methyl group in the general formula (1), 450 ml of 1,4-dioxane, and 19.5 g (263.2 mmol) of calcium hydroxide were added. Into this, 24.5 g (140 mmol) of 4-chlorobenzoyl chloride which corresponds to that $R_2$ is a 4-chlorophenyl group in the general formula (1) was dropped at room temperature. It was heated to 95° C., and stirred under reflux for 2 hours. After allowing it to cool to room temperature, the reaction solution was added to 1,000 ml of 2N aqueous hydrochloric acid and stirred for 1 hour, and then, the precipitated crude crystals were collected by filtration. The obtained crude crystals were dispersed and washed twice with methanol, followed by dispersion washing with ion exchanged water three times. After that, it was dried under reduced pressure overnight at 80° C. to obtain 41.3 g (yield 94.4%) of skin-color crystals.

The structure of the obtained skin-color crystals was identified using NMR. As a result, the following 11 hydrogen signals were detected by 1H-NMR (CDCl$_3$). δ(ppm)= 2.12 (3H), 7.32 (1H), 7.46-7.51 (4H), 7.60 (2H), and 7.86 (1H). It was found that a pyrazolone derivative in which $R_1$ was a phenyl group, $R_2$ was a 4-chlorophenyl group, and $R_3$ was a methyl group in the general formula (1) was obtained. Further, as a result of HPLC analysis, the purity thereof was 100% with the peak area ratio.

Synthesis Example 6 (Synthesis of Example Compound No. 20)

To a 1000 mL four-necked flask that includes a stirrer, a cooling tube, and a thermometer, 12.5 g (40 mmol) of the compound of the synthesis example 5 which corresponds to that $R_1$ is a phenyl group, $R_2$ is a 4-chrolophenyl group, and $R_3$ is a methyl group in the general formula (1), and 850 ml of methanol were added, and the pH thereof was adjusted to pH7 with 6N aqueous ammonia. Into this, 6.4 g (22 mmol) of zinc sulfate dissolved in water was dropped at room temperature. It was heated to 40° C., and stirred for 4 hours. After allowing it to cool to room temperature, the precipitated crude crystals were collected by filtration. The obtained crude crystals were dispersed and washed once with methanol, followed by dispersion washing once with ion exchanged water. The obtained crystals were dried under reduced pressure overnight at 80° C. to obtain 13.3 g (yield 96.2%) of yellow crystals.

The structure of the obtained yellow crystals was identified using NMR. As a result, the following 22 hydrogen signals were detected by 1H-NMR (DMSO-d$_6$). δ(ppm)= 1.63 (6H), 7.11 (2H), 7.32 (4H), 7.41 (4H), 7.53 (4H), and 7.93 (2H). It was found that zinc salt of a pyrazolone derivative in which $R_1$ was a phenyl group, $R_2$ was a 4-chlorophenyl group, and $R_3$ was a methyl group in the general formula (1) was obtained.

Synthesis Example 7 (Synthesis of Example Compound No. 24)

To a 500 mL four-necked flask that includes a stirrer, a cooling tube, and a thermometer, and is purged with nitrogen, 20.9 g (120 mmol) of 1-phenyl-3-methyl-5-pyrazolone which corresponds to that $R_1$ is a phenyl group and $R_3$ is a methyl group in the general formula (1), 400 ml of 1,4-dioxane, and 16.7 g (225 mmol) of calcium hydroxide were added. Into this, 25.0 g (120 mmol) of 4-trifluoromethyl-benzoyl chloride which corresponds to that $R_2$ is a 4-trifluoromethylphenyl group in the general formula (1) was dropped at room temperature. It was heated to 95° C., and stirred under reflux for 2 hours. After allowing it to cool to room temperature, the reaction solution was added to 1,000 ml of 2N aqueous hydrochloric acid and stirred for 1 hour, and then, the precipitated crude crystals were collected by filtration. The obtained crude crystals were dispersed and washed twice with methanol, followed by dispersion washing with ion exchanged water three times. After that, it was dried under reduced pressure overnight at 80° C. to obtain 39.7 g (yield 95.6%) of white crystals.

The structure of the obtained white crystals was identified using NMR. As a result, the following 12 hydrogen signals were detected by 1H-NMR (CDCl$_3$). δ(ppm)=2.34 (3H), 7.31 (1H), 7.49 (2H), 7.68 (2H), 7.83 (2H), and 7.89 (2H). It was found that a pyrazolone derivative in which $R_1$ was a phenyl group, $R_2$ was a 4-trifluoromethylphenyl group, and $R_3$ was a methyl group in the general formula (1) was obtained. Further, as a result of HPLC analysis, the purity thereof was 100% with the peak area ratio.

Synthesis Example 8 (Synthesis of Example Compound No. 25)

To a 1000 mL four-necked flask that includes a stirrer, a cooling tube, and a thermometer, 10.4 g (30 mmol) of the compound of the synthesis example 7 which corresponds to that $R_1$ is a phenyl group, $R_2$ is a 4-trifluoromethylphenyl group, and $R_3$ is a methyl group in the general formula (1), and 600 ml of methanol were added, and the pH thereof was adjusted to pH7 with 6N aqueous ammonia. Into this, 4.8 g (17 mmol) of zinc sulfate dissolved in water was dropped at room temperature. It was heated to 40° C., and stirred for 4 hours. After allowing it to cool to room temperature, the precipitated crude crystals were collected by filtration. The obtained crude crystals were dispersed and washed once with methanol, followed by dispersion washing once with ion exchanged water. The obtained crystals were dried under reduced pressure overnight at 80° C. to obtain 9.5 g (yield 84.0%) of yellow crystals.

The structure of the obtained yellow crystals was identified using NMR. As a result, the following 24 hydrogen signals were detected by 1H-NMR (DMSO-$d_6$). $\delta$(ppm)= 1.58 (6H), 7.12 (2H), 7.33 (4H), 7.59 (4H), 7.84 (4H), and 7.94 (4H). It was found that a pyrazolone derivative in which $R_1$ was a phenyl group, $R_2$ was a 4-trifluoromethylphenyl group, and $R_3$ was a methyl group in the general formula (1) was obtained.

Synthesis Example 9 (Synthesis of Example Compound No. 27)

To a 1000 mL four-necked flask that includes a stirrer, a cooling tube, and a thermometer, 13.2 g (38 mmol) of the compound of the synthesis example 7 which corresponds to that $R_1$ is a phenyl group, $R_2$ is a methyl group in the general formula (1), and 700 ml of methanol were added, and the pH thereof was adjusted to pH7 with 6N aqueous ammonia. Into this, 2.2 g (9.5 mmol) of zirconium chloride dissolved in methanol was dropped at room temperature. It was heated to 40° C., and stirred for 4 hours. After allowing it to cool to room temperature, the precipitated crude crystals were collected by filtration. The obtained crude crystals were dispersed and washed once with methanol, followed by dispersion washing once with ion exchanged water. The obtained crystals were dried under reduced pressure overnight at 80° C. to obtain 11.8 g (yield 84.1%) of yellow crystals.

The structure of the obtained yellow crystals was identified using NMR. As a result, the following 48 hydrogen signals were detected by 1H-NMR (CDCl$_3$). $\delta$(ppm)=1.75 (12H), 7.08 (8H), 7.14 (4H), 7.37 (8H), 7.62 (8H), and 7.89 (8H). It was found that zirconium salt of a pyrazolone derivative in which $R_1$ was a phenyl group, $R_2$ was a 4-trifluoromethylphenyl group, and $R_3$ was a methyl group in the general formula (1) was obtained.

Synthesis Example 10 (Synthesis of Example Compound No. 28)

To a 1000 mL four-necked flask that includes a stirrer, a cooling tube, and a thermometer, and is purged with nitrogen, 34.7 g (142.8 mmol) of 1-(3,4-dichlorophenyl)-3-methyl-5-pyrazolone which corresponds to that $R_1$ is a 3,4-dichlorophenyl group and $R_3$ is a methyl group in the general formula (1), 500 ml of 1,4-dioxane, and 19.9 g (268.6 mml) of calcium hydroxide were added. Into this, 25.0 g (142.8 mmol) of 4-chlorobenzoyl chloride which corresponds to that $R_2$ is 4-chrolophenyl group in the general formula (1) was dropped at room temperature. It was heated to 95° C., and stirred under reflux for 2 hours. After allowing it to cool to room temperature, the reaction solution was added to 1,000 ml of 2N aqueous hydrochloric acid and stirred for 1 hour, and then, the precipitated crude crystals were collected by filtration. The obtained crude crystals were dispersed and washed twice with methanol, followed by dispersion washing with ion exchanged water three times. After that, it was dried under reduced pressure overnight at 80° C. to obtain 49.7 g (yield 91.2%) of brown crystals.

The structure of the obtained brown crystals was identified using NMR. As a result, the following 10 hydrogen signals were detected by 1H-NMR (CDCl$_3$). $\delta$(ppm)=2.10 (3H), 7.50-7.52 (3H), 7.59 (2H), 7.82 (1H), and 8.09 (1H). It was found that a pyrazolone derivative in which $R_1$ was a 3,4-dichlorophenyl group, $R_2$ was a 4-chlorophenyl group, and $R_3$ was a methyl group in the general formula (1) was obtained. Further, as a result of HPLC analysis, the purity thereof was 94.1% with the peak area ratio.

Synthesis Example 11 (Synthesis of Example Compound No. 29)

To a 1000 mL four-necked flask that includes a stirrer, a cooling tube, and a thermometer, 15.3 g (40 mmol) of the compound of the synthesis example 10 which corresponds to that $R_1$ is a 3,4-dichlorophenyl group, $R_2$ is a 4-chlorophenyl group, and $R_3$ is a methyl group in the general formula (1), and 800 ml of methanol were added, and the pH thereof was adjusted to pH7 with 6N aqueous ammonia. Into this, 6.4 g (22 mmol) of zinc sulfate dissolved in water was dropped at room temperature. It was heated to 40° C., and stirred for 4 hours. After allowing it to cool to room temperature, the precipitated crude crystals were collected by filtration. The obtained crude crystals were dispersed and washed once with methanol, followed by dispersion washing once with ion exchanged water. The obtained crystals were dried under reduced pressure overnight at 80° C. to obtain 14.1 g (yield 85.1%) of ocher crystals.

The structure of the obtained ocher crystals was identified using NMR. As a result, the following 20 hydrogen signals were detected by 1H-NMR (THF-$d_8$). $\delta$(ppm)=1.73 (6H), 7.46-7.48 (10H), 8.07 (2H), and 8.43 (2H). It was found that zinc salt of a pyrazolone derivative in which $R_1$ was a 3,4-dichlorophenyl group, $R_2$ was a 4-chlorophenyl group, and $R_3$ was a methyl group in the general formula (1) was obtained.

Synthesis Example 12 (Synthesis of Example Compound No. 32)

To a 500 mL four-necked flask that includes a stirrer, a cooling tube, and a thermometer, and is purged with nitrogen, 20.5 g (84 mmol) of 1-(3,4-dichlorophenyl)-3-methyl-5-pyrazolone which corresponds to that $R_1$ is a 3,4-dichlorophenyl group and $R_3$ is a methyl group in the general formula (1), 400 ml of 1,4-dioxane, and 11.7 g (158 mmol) of calcium hydroxide were added. Into this, 17.6 g (84 mmol) of 4-trifluoromethylbenzoyl chloride which corresponds to that $R_2$ is a 4-trifluoromethylphenyl group in the general formula (1) was dropped at room temperature. It was heated to 95° C., and stirred under reflux for 2 hours. After allowing it to cool to room temperature, the reaction solution was added to 1,000 ml of 2N aqueous hydrochloric acid and stirred for 1 hour, and then, the precipitated crude crystals were collected by filtration. The obtained crude crystals were dispersed and washed twice with methanol, followed by dispersion washing with ion exchanged water three times. After that, it was dried under reduced pressure overnight at 80° C. to obtain 29.8 g (yield 85.2%) of brownish-white crystals.

The structure of the obtained brownish-white crystals was identified using NMR. As a result, the following 10 hydrogen signals were detected by 1H-NMR (THF-$d_8$). $\delta$(ppm)= 2.04 (3H), 7.64 (1H), 7.88-7.94 (5H), and 8.16 (1H). It was found that a pyrazolone derivative in which $R_1$ was a 3,4-dichlorophenyl group, $R_2$ was a 4-trifluoromethylphenyl group, and $R_3$ was a methyl group in the general formula (1)

was obtained. Further, as a result of HPLC analysis, the purity thereof was 93.5% with the peak area ratio.

Synthesis Example 13 (Synthesis of Example Compound No. 33)

To a 1000 mL four-necked flask that includes a stirrer, a cooling tube, and a thermometer, 7.5 g (18 mmol) of the compound of the synthesis example 12 which corresponds to that $R_1$ is a 3,4-dichlorophenyl group, $R_2$ is a 4-trifluoromethylphenyl group, and $R_3$ is a methyl group in the general formula (1), and 400 ml of methanol were added, and the pH thereof was adjusted to pH7 with 6N aqueous ammonia. Into this, 2.9 g (10 mmol) of zinc sulfate dissolved in water was dropped at room temperature. It was heated to 40° C., and stirred for 4 hours. After allowing it to cool to room temperature, the precipitated crude crystals were collected by filtration. The obtained crude crystals were dispersed and washed once with methanol, followed by dispersion washing once with ion exchanged water. The obtained crystals were dried under reduced pressure overnight at 80° C. to obtain 6.1 g (yield 76.4%) of yellowish white crystals.

The structure of the obtained yellowish white crystals was identified using NMR. As a result, the following 20 hydrogen signals were detected by 1H-NMR (THF-$d_8$). δ(ppm)= 1.79 (6H), 7.55 (2H), 7.71 (4H), 7.85 (4H), 8.13 (2H), and 8.48 (2H). It was found that zinc salt of a pyrazolone derivative in which $R_1$ was a 3,4-dichlorophenyl group, $R_2$ was a 4-trifluoromethylphenyl group, and $R_3$ was a methyl group in the general formula (1) was obtained.

Synthesis Example 14 (Synthesis of Example Compound No. 35)

To a 1000 mL four-necked flask that includes a stirrer, a cooling tube, and a thermometer, 7.8 g (19 mmol) of the compound of the synthesis example 12 which corresponds to that $R_1$ is a 3,4-dichlorophenyl group, $R_2$ is a 4-trifluoromethylphenyl group, and $R_3$ is a methyl group in the general formula (1), and 400 ml of methanol were added, and the pH thereof was adjusted to pH7 with 6N aqueous ammonia. Into this, 1.1 g (4.7 mmol) of zirconium chloride dissolved in methanol was dropped at room temperature. It was heated to 40° C., and stirred for 4 hours. After allowing it to cool to room temperature, the precipitated crude crystals were collected by filtration. The obtained crude crystals were dispersed and washed once with methanol, followed by dispersion washing once with ion exchanged water. The obtained crystals were dried under reduced pressure overnight at 80° C. to obtain 6.5 g (yield 78.9%) of ocher crystals.

The structure of the obtained ocher crystals was identified using NMR. As a result, the following 40 hydrogen signals were detected by 1H-NMR (CDCl$_3$). δ(ppm)=1.88 (12H), 7.21 (4H), 7.62 (8H), 7.81 (8H), 7.90 (4H), and 8.29 (4H). It was found that zirconium salt of a pyrazolone derivative in which $R_1$ was a 3,4-dichlorophenyl group, $R_2$ was a 4-trifluoromethylphenyl group, and $R_3$ was a methyl group in the general formula (1) was obtained.

Synthesis Examples 15 to 28

In synthesis examples 15 to 28, pyrazolone derivatives shown as example compound No. 39, 49, 50 to 52, 61, 64, 67, 71, 73, 78, 91, 93, and 95 in Table 1 and 2, and metal salts thereof were synthesized.

Environmental Charge Stability of Charge Control Agent

Method of Measuring Charge Amount

After causing the above-mentioned synthesized charge control agent to charge by using a blow-off charge amount measuring machine (TB-200-type, manufactured by Toshiba Chemical Co., Ltd.), the initial charge amount and the saturated charge amount in each environment were measured.

The conditions for measuring the blow-off charge amount are as follows.

Developer amount: 0.2000 g±0.005 g

Blowing time: 60 s $N_2$ blow pressure: 0.2 kgf/cm$^2$ (silicon coat F96-150)

T/C=4%

Rotation speed of ball mill: 110 rpm.

Further, in order to evaluate the environmental stability, evaluation samples (the synthesized 4-acyl-5-pyrazolone derivative described above) are placed in a thermo-hygrostat (HPCC-120-20HK, manufactured by Isuzu Seisakusho) set in the measurement environment for 24 hours. They are caused to charge for 30 minutes using a ball mill placed in the thermos-hygrostat. Specifically, the saturated charge amount after exposure to the environment under an atmosphere of a temperature of 10° C. and a humidity of 30% (in an LL environment), an atmosphere of a temperature of 25° C. and a humidity of 50% (in an NN environment), or an atmosphere of a temperature of 35° C. and a humidity of 85% (in an HH environment), for 24 hours was measured. For "the saturated charge amount in the LL environment" and "the saturated charge amount in the HH environment", the changes (L/N ratio and H/N ratio) with respect to "the saturated charge amount in the NN environment" were obtained. The measurement results of the environmental charge stability of the synthesis examples 2, 4, 6, 7 to 9, and 11 to 28 are shown in Table 3.

Comparative Compound

For comparison, the chargeability in each environment was measured using the commercially available charge control agent (BONTRON E-88, Orient Chemical Industries Co., Ltd.) represented by the following structural formula as a comparative compound, by the above-mentioned measuring method. For "the saturated charge amount in the LL environment" and "the saturated charge amount in the HH environment", the changes (L/N ratio and H/N ratio) with respect to "the saturated charge amount in the NN environment" were obtained. The measurement results of the environmental charge stability of the comparative compound are shown in Table 3.

[Chem. 6]

(Comparative compound)

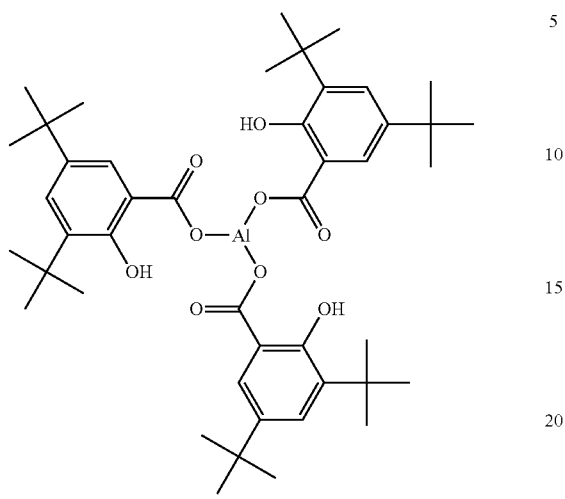

TABLE 3

| Synthesis example | Compound | Environmental charge stability of CCA (μC/g) | | | L/N | H/N |
|---|---|---|---|---|---|---|
| | | LL environment | NN environment | HH environment | | |
| Synthesis example 2 | Example compound No. 2 | −159.5 | −138.5 | −109.9 | 1.2 | 0.8 |
| Synthesis example 4 | Example compound No. 4 | −104.5 | −104.3 | −83.7 | 1.0 | 0.8 |
| Synthesis example 6 | Example compound No. 20 | −184.6 | −174.3 | −131.6 | 1.1 | 0.8 |
| Synthesis example 7 | Example compound No. 24 | −120.3 | −108.6 | −89.9 | 1.1 | 0.8 |
| Synthesis example 8 | Example compound No. 25 | −134.9 | −142.4 | −109.9 | 0.9 | 0.8 |
| Synthesis example 9 | Example compound No. 27 | −93.2 | −102.1 | −74.1 | 0.9 | 0.7 |
| Synthesis example 11 | Example compound No. 29 | −85.0 | −81.3 | −71.0 | 1.0 | 0.9 |
| Synthesis example 12 | Example compound No. 32 | −68.5 | −65.4 | −55.8 | 1.0 | 0.9 |
| Synthesis example 13 | Example compound No. 33 | −60.8 | −87.9 | −91.9 | 0.7 | 1.0 |
| Synthesis example 14 | Example compound No. 35 | −107.6 | −108.1 | −148.7 | 1.0 | 1.4 |
| Synthesis example 15 | Example compound No. 39 | −78.0 | −68.3 | −50.1 | 1.1 | 0.7 |
| Synthesis example 16 | Example compound No. 49 | −178.4 | −140.2 | −58.6 | 1.3 | 0.4 |
| Synthesis example 17 | Example compound No. 50 | −150.6 | −138.6 | −102.3 | 1.1 | 0.7 |
| Synthesis example 18 | Example compound No. 51 | −57.2 | −40.5 | −3.0 | 1.4 | 0.1 |
| Synthesis example 19 | Example compound No. 52 | −129.0 | −121.8 | −68.6 | 1.1 | 0.6 |
| Synthesis example 20 | Example compound No. 61 | −150.7 | −140.9 | −104.9 | 1.1 | 0.7 |
| Synthesis example 21 | Example compound No. 64 | −123.5 | −136.5 | −133.4 | 0.9 | 1.0 |
| Synthesis example 22 | Example compound No. 67 | −71.6 | −71.0 | −66.0 | 1.0 | 0.9 |
| Synthesis example 23 | Example compound No. 71 | −105.3 | −118.9 | −92.9 | 0.9 | 0.8 |
| Synthesis example 24 | Example compound No. 73 | −96.2 | −103.6 | −98.1 | 0.9 | 0.9 |
| Synthesis example 25 | Example compound No. 78 | −24.6 | −30.3 | −22.0 | 0.8 | 0.7 |
| Synthesis example 26 | Example compound No. 91 | −172.1 | −219.4 | −81.1 | 0.8 | 0.4 |

TABLE 3-continued

| Synthesis example | Compound | Environmental charge stability of CCA (μC/g) | | | | |
|---|---|---|---|---|---|---|
| | | LL environment | NN environment | HH environment | L/N | H/N |
| Synthesis example 27 | Example compound No. 93 | −193.2 | −187.7 | −163.6 | 1.0 | 0.9 |
| Synthesis example 28 | Example compound No. 95 | −167.2 | −147.8 | −121.3 | 1.1 | 0.8 |
| | Comparative compound | −68.4 | −94.9 | −73.3 | 0.7 | 0.8 |

Preparation of Suspension Polymerization Toner

Example 1

(Preparation of Aqueous Medium)

In a tall beaker, 382 parts of ion exchanged water and 157 parts of $Na_3PO_4$ aqueous solution of 0.3 mol/L were placed. They were kept at 60° C. with a water bath while being stirred at 3,200 rpm by using a high-speed stirring apparatus, Ultra Turrax. After increasing the rotation speed of the stirrer to 10,000 rpm, 28 parts of $CaCl_2$ aqueous solution of 3.0 mol/L was gradually added thereto to prepare an aqueous dispersion medium (3E-3) including a fine water-insoluble dispersion stabilizer, $Ca_3(PO_4)_2$.

To a container made of PP, 19.1 parts of styrene monomer, 8.1 parts of n-butyl acrylate, 0.3 parts of cyan pigment (Pigment Blue 15:3), 1.5 parts of polyester resin (ER-561 manufactured by Mitsubishi Rayon Co., Ltd.), 0.9 parts of pyrazolone derivative in the synthesis example 1 (example compound No. 1), and zirconia beads (particle size of beads: 0.65 mmφ, the amount corresponding to 15 ml) were added. They were dispersed for 3 hours with a paint conditioner (Red Devil No. 5400-5L manufactured by UNION N.J. (USA)). Zirconia beads were removed using a sieve to form an oil layer. One part of polymerization initiator, 2,2′-azobis(2,4-dimethylvaleronitrile), was added thereto, and a water layer obtained by adding 44 g of purified water to 36.5 parts of the above-mentioned aqueous dispersion medium, 3E-3, was formed. The inner temperature was kept at 70° C., and granulation was performed by stirring them at 7000 rpm using Ultra Turrax. Polymerization was performed for 5 hours under a nitrogen atmosphere at the reaction temperature of 80° C. After completion of the reaction, 35% hydrochloric acid was added thereto to adjust the PH to 1 to 2. After that, filtration, washing with water, and then drying at 40° C. were performed to obtain a polymerized toner. The obtained toner was sieved with a sieve of 166 mesh (sieve opening of 90 μm) to obtain a toner for evaluation.

Evaluation of Charging

After mixing and shaking 2 parts of obtained toner for evaluation and 100 parts of silicon-based ferrite carrier (F96-150 manufactured by Powdertech co., Ltd.), the toner is negatively charged using the above-mentioned method of measuring the charge amount. After that, the saturated charge amount was evaluated by a blow-off powder charge amount measuring apparatus. The measurement environment conditions were the above-mentioned environment conditions. The results are summarized in Table 4.

Example 2

A toner was prepared under the same conditions as those in example 1 except that the pyrazolone derivative of the synthesis example 1 was replaced with the zinc salt (example compound No. 2) of the pyrazolone derivative of the synthesis example 2. The saturated charge amount in each environment was measured, and the environmental stability (L/N ratio and H/N ratio) was evaluated. The results are summarized in Table 4.

Example 3

A toner was prepared under the same conditions as those in example 1 except that the pyrazolone derivative of the synthesis example 1 was replaced with the pyrazolone derivative (example compound No. 28) of the synthesis example 10. The saturated charge amount in each environment was measured, and the environmental stability (L/N ratio and H/N ratio) was evaluated. The results are summarized in Table 4.

Example 4

A toner was prepared under the same conditions as those in example 1 except that the pyrazolone derivative of the synthesis example 1 was replaced with the zinc salt (example compound No. 29) of the pyrazolone derivative of the synthesis example 11. The saturated charge amount in each environment was measured, and the environmental stability (L/N ratio and H/N ratio) was evaluated. The results are summarized in Table 4.

Example 5

A toner was prepared under the same conditions as those in example 1 except that the pyrazolone derivative of the synthesis example 1 was replaced with the zinc salt (example compound No. 25) of the pyrazolone derivative of the synthesis example 8. The saturated charge amount in each environment was measured, and the environmental stability (L/N ratio and H/N ratio) was evaluated. The results are summarized in Table 4.

Example 6

A toner was prepared under the same conditions as those in example 1 except that the pyrazolone derivative of the synthesis example 1 was replaced with the zirconium salt (example compound No. 27) of the pyrazolone derivative of the synthesis example 9. The saturated charge amount in each environment was measured, and the environmental stability (L/N ratio and H/N ratio) was evaluated. The results are summarized in Table 4.

Example 7

A toner was prepared under the same conditions as those in example 1 except that the pyrazolone derivative of the synthesis example 1 was replaced with the zinc salt (example compound No. 33) of the pyrazolone derivative of the synthesis example 13. The saturated charge amount in each environment was measured, and the environmental stability (L/N ratio and H/N ratio) was evaluated. The results are summarized in Table 4.

Example 8

A toner was prepared under the same conditions as those in example 1 except that the pyrazolone derivative of the synthesis example 1 was replaced with the zirconium salt (example compound No. 35) of the pyrazolone derivative of the synthesis example 14. The saturated charge amount in each environment was measured, and the environmental stability (L/N ratio and H/N ratio) was evaluated. The results are summarized in Table 4.

Comparative Example 1

For comparison, a comparative suspension polymerization toner was prepared under the same conditions as those in example 1 except that the pyrazolone derivative of the synthesis example 1 was replaced with the comparative compound represented by the above-mentioned structural formula. By using a blow-off powder charge amount measuring apparatus, the saturated charge amount in each environment was measured, and the environmental stability (L/N ratio and H/N ratio) was evaluated. The results are summarized in Table 4.

TABLE 4

| | Charge amount in NN environment (µC/g) | L/N ratio | H/N ratio |
| --- | --- | --- | --- |
| Example 1 | −13.22 | 1.4 | 0.4 |
| Example 2 | −15.53 | 1.3 | 0.5 |
| Example 3 | −11.30 | 1.5 | 0.7 |
| Example 4 | −17.46 | 1.2 | 0.6 |
| Example 5 | −10.25 | 1.4 | 0.1 |
| Example 6 | −10.61 | 1.4 | 0.1 |
| Example 7 | −12.69 | 1.5 | 0.3 |
| Example 8 | −12.44 | 1.2 | 0.3 |
| Comparative example 1 | −9.06 | 1.6 | 0.4 |

As is clear from the results in Table 3, the charge control agent including the pyrazolone derivative represented by the general formula (1) in the present invention or the salt of the derivative as an active ingredient shows a charge amount higher than that of an existing charge control agent. Further, when comparing the saturated charge amount under conditions of high temperature and high humidity (H/H) (a temperature of 35° C. and a humidity of 85%) or under conditions of low temperature and low humidity (L/L) (a temperature of 10° C. and a humidity of 30%) and the saturated charge amount under an normal environment (under an atmosphere of a temperature of 25° C. and a humidity of 50%), since the change is smaller than that of the comparative compound, it is excellent in the environmental stability.

As is clear from the results in Table 4, the suspension polymerization toner using the charge control agent including the pyrazolone derivative represented by the general formula (1) in the present invention or the salt of the derivative as an active ingredient shows a charge amount higher than that of a toner using an existing charge control agent, and is excellent in the charging environmental stability of the toner.

Specifically, the charge control agent including the pyrazolone derivative in the present invention or the salt of the derivative as an active ingredient, which is complexly colorless, has a large charge amount, and is capable of imparting charging performance higher and more stable than that of an existing charge control agent by the characteristics of the excellent environmental stability of charging, in the case where it is used for color toners, particularly in polymerized toners. Further, it is possible to use a safer pyrazolone derivative or a salt thereof to produce an environmentally safe toner by performing a metallization reaction using nontoxic metal ions or not performing a metallization reaction.

The charge control agent including the pyrazolone derivative in the present invention or the salt of the derivative as an active ingredient is excellent in charge control characteristics, resistance to environment, and durability. Even when the concentration of a charge control agent using the pyrazolone derivative or the salt of the derivative according to the present invention is low, i.e., not more than 1.0% by mass, the charge control agent can give a significantly large charge amount in the case where it is used for a toner. Therefore, it is possible to obtain an image having no fog and favorable image concentration, dot reproducibility and fine line reproducibility. It is possible to contribute to miniaturization of a copying machine or printer, speeding up, shortening of the waiting time, and reduction in the amount of the charge control agent to be used. Further, since it is excellent in the environmental change stability, it allows the use of copying machines under the same specifications also in regions and countries with different climatic conditions beyond national boundaries. Further, the pyrazolone derivative charge control agent according to the present invention can be applied also to usage for which using no metal is required.

The invention claimed is:
1. A toner, comprising:
a charge control agent including a pyrazolone derivative or a salt of the derivative as an active agent;
a coloring agent; and
a binder resin,
wherein the derivative is represented by the following general formula (1):

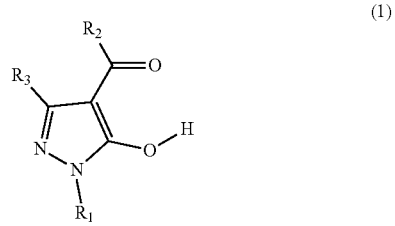

(1)

in the formula, $R_1$, $R_2$, and $R_3$ each independently represent a substituted or unsubstituted C1 to C20 linear or branched alkyl group, a substituted or unsubstituted aromatic hydrocarbon group, a substituted or unsubstituted aromatic heterocyclic group, or a substituted or unsubstituted condensed polycyclic aromatic group, and wherein a volume average particle size of the charge control agent is in a range of 0.1 µm to 20 µm.

2. The toner according to claim 1, wherein in the general formula (1), $R_1$, $R_2$, and $R_3$ each independently represent a substituted or unsubstituted aromatic hydrocarbon group, a substituted or unsubstituted aromatic heterocyclic group, or a substituted or unsubstituted condensed polycyclic aromatic group.

3. The toner according to claim 1, wherein in the general formula (1), $R_1$, $R_2$, and $R_3$ each independently represent a substituted or unsubstituted aromatic hydrocarbon group.

4. The toner according to claim 1, wherein the salt of the pyrazolone derivative is a zinc (Zn) salt, an aluminum (Al) salt, a zirconium (Zr) salt, an iron (Fe) salt, a barium (Ba) salt, or a vanadium (V) salt.

* * * * *